US012741991B2

(12) United States Patent
Boudewijns et al.

(10) Patent No.: US 12,741,991 B2
(45) **Date of Patent: *Sep. 22, 2026**

(54) LIVE-ATTENUATED FLAVIVIRUSES WITH HETEROLOGOUS ANTIGENS

(71) Applicant: Katholieke Universiteit Leuven, Leuven (BE)

(72) Inventors: Robbert Boudewijns, Essen (BE); Kai Dallmeier, Kessel-Lo (BE); Johan Neyts, Kessel-Lo (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/312,927

(22) Filed: May 5, 2023

(65) Prior Publication Data

US 2023/0406889 A1 Dec. 21, 2023

Related U.S. Application Data

(63) Continuation of application No. 16/753,364, filed as application No. PCT/EP2018/077157 on Oct. 5, 2018, now Pat. No. 11,680,084.

(30) Foreign Application Priority Data

Oct. 5, 2017 (GB) ..................................... 1716254

(51) Int. Cl.
*C07K 14/005* (2006.01)
*A61K 39/00* (2006.01)

(52) U.S. Cl.
CPC ........ *C07K 14/005* (2013.01); *A61K 2039/53* (2013.01); *A61K 2039/572* (2013.01); *C07K 2319/00* (2013.01); *C12N 2770/24121* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 2008/0318208 A1 | 12/2008 | Puffer et al. | |
| 2013/0156818 A1 | 6/2013 | de los Rios et al. | |

FOREIGN PATENT DOCUMENTS

| | | | |
|---|---|---|---|
| WO | 2005042014 A1 | 5/2005 | |
| WO | 2008076290 A2 | 6/2008 | |
| WO | 2014174078 A1 | 10/2014 | |

OTHER PUBLICATIONS

Min et al., Prevention and Management of Viral Hepatitis in Primary Care, 2025, Topics in Antiviral Medicine, vol. 33, No. 6, pp. 711-726.*
International Search Report in reference to co-pending European Patent Application No. PCT/EP2018/077157 filed Oct. 5, 2018.
International Search Report and Written Opinion in reference to co-pending European Patent Application No. PCT/EP2018/077157 filed Oct. 5, 2018.
Stoyanov C T et al: Immunogenicity and protective efficacy of a recombinant yellow fever vaccine against the murine malarial parasite Plasmodium yoelii11 , Vaccine, Els Ev I Er, Amsterdam, vol. 28, No. 29, pp. 4644-4652, Jun. 23, 2010, XP027474780.
Rasala Beth A et al: "Robust Expression and Secretion of Xylanasel in Chlamydomonas reinhardtii by Fusion to a Selection Gene and Processing with the FMDV 2A Peptide", PLOS ONE, vol. 7, No. 8, Aug. 1, 2012, XP002688993.
Weniger, et al., "Alternative vaccine delivery methods", Section Three: Vaccines in development and new vaccine strategies, pp. 1200-1231, 6th addition, 2013.
Bonaldo, et al., "The yellow fever 17D virus as a platform for new live attenuated vaccines", Human Vaccines & Immunotherapeutics, pp. 1256-1265, May 2014.
Chng, et al., "Cleavage efficient 2A peptides for high level monoclonal antibody expression in CHO cells", Bioprocessing Technology Institute, vol. 7, Issue 2, pp. 403-412, 2015.
Cicin-Sain, et al., "Vaccination of Mice with Bacteria Carrying a Cloned Herpesvirus Genome Reconstituted in Vivo", Journal of Virology, vol. 77, No. 15, pp. 8249-8255, Aug. 2003.
Darji, et al., "Oral delivery of DNA vaccines using attenuated *Salmonella typhimurium* as carrier", FEMS Immunology and Medical Microbiology, vol. 27, pp. 341-349, 2000.
Donnelly, et al., "The 'cleavage' activities of foot-and-mouth disease virus 2A site-directed mutants and naturally occurring '2A-like' sequences", Journal of General Virology, vol. 82, pp. 1027-1041, 2001.
Fischl, et al., "High-thoughput Screening Using Dengue Virus Reporter Genomes", Chapter 17, vol. 1030, pp. 205-219, 2013.
Jung, et al., "Activation of a Heterogenous Hepatitis B (HB) Core and e Antigen-Specific CD4+ T-Cell Population during Seroconversion to Anti-HBe and Anti-HBs in Hepatitis B Virus Infection", vol. 69, No. 6, pp. 3358-3368, Jun. 1995.

(Continued)

*Primary Examiner* — Benjamin P Blumel
(74) *Attorney, Agent, or Firm* — DINSMORE & SHOHL LLP

(57) ABSTRACT

The invention relates to polynucleotides comprising the sequence of a flavivirus preceded by a sequence encoding an N terminal part of a flavivirus Capsid protein, an immunogenic protein, or a part thereof comprising a an immunogenic peptide, and a 2A cleaving peptide, and to the virus encoded by such sequences. The invention further relates to the use of such polynucleotides and viruses as vaccines.

43 Claims, 6 Drawing Sheets

Figure 1:
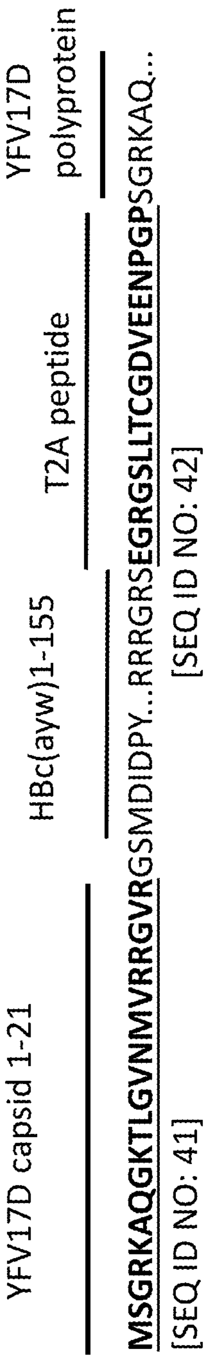

Specification includes a Sequence Listing.

(56) References Cited

OTHER PUBLICATIONS

Samsa, et al., "Uncoupling cis-Acting RNA Elements from Coding Sequences revealed a Requirement of the N-Terminal Region of Dengue Virus Capsid Protein in Virus Particle Formation", Journals of Virology, vol. 86, No. 2, pp. 1046-1058, Jan. 2012.
Schoggins, et al., "Dengue reporter viruses reveal viral dynamics in interferon effectors in vitro", vol. 109, No. 36, pp. 14610-14615, Sep. 4, 2012.
Thimme, et al., "CD8+ T Cells Mediate Viral Clearance and Disease Pathogenesis during Acute Hepatitis B Virus Infection", Journal of Virology, vol. 77, No. 1, pp. 68-76, Jan. 2003.
Saltzman, et al., DNA Vaccines, Methods and Protocols, Methods in Molecular Medicin E, Second Edition, vol. 127, pp. 71-136, 2014.

* cited by examiner

A

B

A

B

LIVE-ATTENUATED FLAVIVIRUSES WITH HETEROLOGOUS ANTIGENS

CROSS-REFERENCES TO RELATED APPLICATIONS

This application is a continuation of U.S. patent application Ser. No. 16/753,364, which is a national stage application under 35 U.S.C. § 371 of International Application No. PCT/EP2018/077157, filed Oct. 5, 2018, which International Application claims priority of benefit to Great British Patent Application No. 1716254.6, filed Oct. 5, 2017. The entireties of each of U.S. patent application Ser. No. 16/753,364, International Application No. PCT/EP2018/077157, and Great British Patent Application No. 1716254.6 are hereby incorporated herein by reference.

INCORPORATION OF SEQUENCE LISTING

A computer-readable form (CRF) sequence listing having file name ASB0001NA.xml (35,803 bytes), created May 4, 2023, is incorporated herein by reference. The nucleic acid sequences and amino acid sequences listed in the accompanying sequence listing are shown using standard abbreviations as defined in 37 C.F.R. § 1.822.

BACKGROUND OF THE INVENTION

Hepatitis B virus (HBV) is the causative agent of hepatitis B, a liver disease that can evolve to chronicity. Complications of chronic hepatitis B include liver cirrhosis and hepatocellular carcinoma or liver cancer. An estimated 240 million people, mainly in Asia and Africa, are chronically infected with HBV, with more than 686.000 people dying every year due to complications related to chronic HBV infection. HBV is a member of the Hepadnaviridae, a family of retrotranscribing viruses with partially double-stranded genomic DNA. It is most commonly transmitted perinatally from an infected mother, or horizontally through unprotected sexual activities or intravenous drug use.

Upon infection of a hepatocyte by HBV, the HBV nucleocapsid is transported to the nucleus. There, the genetic material is repaired and retained as a mini-chromosome (cccDNA) in the nucleus of the cell where it functions as a reservoir.

Most patients control an acute infection efficiently without the appearance of any evident clinical symptoms. However, 5-10% of infected adults (and >90% of infected neonates) are unable to clear the virus and develop chronic hepatitis B. In those who clear the virus, vigorous and multispecific CD4 and CD8 T-cell responses of the Th1 profile (production of IFN-γ) are detected The CD4 T-cell response that is specific for the HBV nucleocapsid protein [also called HBV core antigen (HBcAg or HBc)] is important in HBV control since this stimulates the activation of CD8 T-cells [Jung et al. (1995) *J. Virol.* 69, 3358-3368]. In fact, CD8 T-cells, (or CTLs) are the main cellular subset responsible for resolution of the infection as they clear HBV-infected hepatocytes through cytolytic and non-cytolytic mechanisms. In those who do not resolve the infection and develop chronic hepatitis B, the responses are weaker. Indeed, it has been demonstrated that the level of HBV-specific CTLs is correlated to HBV control [Thimme et al. (2003) *J. Virol.* 77, 68-76].

The restoration of a strong CTL response is the main goal of a therapeutic HBV vaccine. Such vaccine is urgently awaited so as to be able to cure millions of people with chronic hepatitis B. The yellow fever vaccine (strain 17D) is one of the safest and most effective vaccines currently available. About 99% of those vaccinated (after a single dose) develop life-long immunity within days to weeks. The vaccine came into use in 1938 and since then over 600 million doses have been dispensed. It is important to note that the YFV 17D vaccine does not only induce potent neutralizing antibodies but also (i) strong and broadly directed CD8+ T-cell responses, (ii) exceptionally strong memory T-cell responses as well as (iii) a potent activation of the innate immune system, especially of dendritic cells. Such characteristics may provide the ideal context for the construction therapeutic vaccines against chronic infections such as those caused by the hepatitis B virus.

Attempts have been made to clone antigens upstream of a yellow fever to obtain a fusion protein, whereby the antigen is released from the viral protein, using a protease signal peptide and an ubiquitin cleavage site [Schoggins et al. (2012) *Proc NatlAcadSci USA.* 109, 14610-14615.].

However as indicated in the review article of Bonaldo et al. (2014) *Hum. Vaccine. Immunother* 10, 1256-1265). such constructs lose the heterologous genes after a few passages. Alternative constructs are required to overcome the genetic instability.

SUMMARY OF THE INVENTION

The invention relates to polynucleotides comprising the sequence of a Yellow Fever virus wherein the nucleotide sequence encoding said Yellow Fever virus is preceded by an N terminal part of the yellow fever virus Capsid protein followed by a T cell antigen, or a part thereof comprising a T cell antigen, and the sequence encoding for the *Thosea asigna* 2A peptide.

Typically the nucleotide sequence of the N terminal part of the capsid gene has one or more synonymous codons compared with the corresponding sequence in the full length yellow fever virus sequence.

In an embodiment, the terminal part of the Yellow Fever virus capsid encodes for a peptide consisting of the sequence MSGRKAQGKTLGVNMVRRGVR (SEQ ID NO:2).

In an embodiment, the *Thosea asigna* 2A peptide has the sequence EGRGSLLTCGDVEENPGP (SEQ ID NO:16).

In an embodiment, the amino acid C terminal of the T2A peptide is Gly, Ala, Ser or Thr.

In an embodiment wherein the codon usage of the antigen is adapted for expression in bacteria.

In an embodiment the sequences with synonymous codons are:

```
                                        (SEQ ID NO: 14)
atgtctggtcgtaaagctcagggaaaaaccct

gggcgtcaatatggtacgacgaggagttcgc
and
                                        (SEQ ID NO: 15)
agcggccgcaaagcccagggtaagacactggg

cgtgaacatggttcgtcgcggcgtccgg.
```

In an embodiment, the Yellow Fever virus is the YF 17D attenuated virus.

In an embodiment, the polynucleotide is an Bacterial Artificial Chromosome.

In an embodiment, the BAC comprises an inducible bacterial ori sequence for amplification of said BAC to more than 10 copies per bacterial cell, and a viral expression cassette comprising a cDNA of said polynucleotide and comprising cis-regulatory elements for transcription of said viral cDNA in mammalian cells and for processing of the transcribed RNA into infectious RNA virus.

In an embodiment, said T cell antigen is selected from the group consisting of the core antigen of HBC, OVA and EBNA1, namely the encoded T cell antigen comprises the amino acid sequence of SEQ ID NO:3, or a fragment thereof comprising a T cell epitope, the encoded T cell antigen comprises the amino acid sequence of SEQ ID NO:7 or a fragment thereof comprising a T cell epitope, the encoded T cell antigen comprises the amino acid sequence of SEQ ID NO:10 or a fragment thereof comprising a T cell epitope; the encoded T cell antigen compromises the amino acid sequence of SEQ ID NO:13.

Such polynucleotides can be used as a vaccine, more particular for use as a vaccine in the prevention of an infection caused by said T cell antigen or partial T cell epitope.

Furthermore, the above polynucleotides can be used as a vaccine in the simultaneous prevention of an infection caused by said T cell antigen or partial T cell epitope and of a Yellow Fever infection.

Herein disclosed are methods of preparing a vaccine against a T cell antigen, comprising the steps of:

(a) providing a BAC which comprises an inducible bacterial ori sequence for amplification of said BAC to more than 10 copies per bacterial cell, and a viral expression cassette comprising a cDNA of a polynucleotide as described above, and comprising cis-regulatory elements for transcription of said viral cDNA in mammalian cells and for processing of the transcribed RNA into infectious RNA virus (b) transfecting mammalian cells with the BAC of step (a)

(c) validating replicated virus of the transfected cells of step (b) for virulence and the capacity of generating antibodies against said T cell antigen, cloning the virus validated in step (c) into a vector, formulating the vector into a vaccine formulation.

Herein the vector is a BAC, can comprises an inducible bacterial ori sequence for amplification of said BAC to more than 10 copies per bacterial cell.

The present invention is equally applicable to other flaviviruses wherein T cell antigens are cloned N terminal of the capsid protein.

The present invention is equally applicable to chimeric yellow fever strains wherein the prME genes of the YFV are replaced by those of other flaviviruses such as Japanese Encephalitis or Dengue.

The invention is further summarized in the following statements:

1. A polynucleotide comprising the sequence of a flavivirus characterized in that the nucleotide sequence encoding said flavivirus is preceded by a sequence encoding:

a part of a flavivirus Capsid protein comprising or consisting of the N terminal part of the flavivirus Capsid protein, an immunogenic protein, or a part thereof comprising an immunogenic peptide, and a 2A cleaving peptide.

For the purpose of vaccination, these flavivirusses are typically life infectious attenuated viruses.

2. The polynucleotide according to statement 1, wherein the part of the flavivirus Capsid protein comprises or consists of the 21 N terminal amino acids of the flavivirus Capsid protein.

The embodiment of 21 AA is based on the examples performed with YFV but may differ depending of the type of flavivirus and can be as short as 16 amino acids for Japanese Encephalitis virus.

Apart from the minimal essential N terminus of 16 to 21 amino acids, depending from the flavivirus considered, the chimeric virus may comprise prior the site of insertion a further part of the capsid protein, such that the N terminal fragment of the capsid may have a length of 25, 30, 35, 40 or 50 amino acids, since a Dengue virus constructs with an N terminal fragment of 34 amino acids have been described (Fischl & Bartenschlager (2013) *Methods Mol. Biol.* 1030, 205-219.

3. The polynucleotide according to statement 1 or 2, wherein the nucleotide sequence encoding the N terminal part of the capsid gene has one or more synonymous codons compared with the corresponding sequence in the full length viral sequence.
4. The polynucleotide according to statement 1, 2, or 3 wherein the flavivirus is yellow fever virus.
5. The polynucleotide according to any one of statements 1 to 4, where the terminal part of the Yellow Fever virus capsid consist of the sequence MSGRKAQGKTLGVNMVRRGVR (SEQ ID NO:2).
6. The polynucleotide according to any one of statements 1 to 5, wherein the 2A cleaving peptide comprises the sequence DXEXNPGP [SEQ ID NO:46].
7. The polynucleotide according to any one of statements 1 to 5, wherein the 2A cleaving peptide comprises the sequence LxxxGDVExPGP [SEQ ID NO:17].
8. The polynucleotide according to any one of statements 1 to 7, wherein the 2A cleaving peptide comprises the sequence LLTCGDVEENPGP [SEQ ID NO:18].
9. The polynucleotide according to any one of statements 1 to 8, wherein the 2A cleaving peptide is the *Thosea asigna* 2A peptide with amino acid sequence

```
                                    (SEQ ID NO: 16)
EGRGSLLTCGDVEENPGP.
```

10. The polynucleotide according to any one of statements 1 to 9, wherein the amino acid C terminal of the 2A cleaving peptide is Gly, Ala, Ser or Thr.
11. The polynucleotide according to any one of statements 1 to 10, wherein the immunogenic protein is a T cell antigen and the immunogenic fragment thereof comprises a T cell epitope.
12. The polynucleotide according to any one of statements 1 to 11, wherein the nucleotide sequence encoding the capsid protein 5' of the sequence encoding said immunogenic protein or fragment thereof has the nucleotide sequence of the wild type flavivirus.
13. The polynucleotide according to any one of statements 1 to 11, wherein the codon usage of the immunogenic protein of immunogenic fragment thereof is adapted for expression in bacteria.
14. The polynucleotide according to any one of statements 1 to 12, wherein the sequences with synonymous codons are:

```
                                    (SEQ ID NO: 14)
atgtctggtcgtaaagctcagggaaaaaccct

gggcgtcaatatggtacgacgaggagttcgc
and
```

-continued (SEQ ID NO: 15)

agcggccgcaaagcccagggtaagacactggg cgtgaacatggttcgtcgcggcgtccgg.

15. The polynucleotide according to any one of statements 1 to 14, wherein the Yellow Fever virus is the YF 17D attenuated virus.

16. The polynucleotide according to any one of statements 1 to 15, which is an Bacterial Artificial Chromosome.

17. The polynucleotide according to statement 16, wherein the BAC comprises an inducible bacterial ori sequence for amplification of said BAC to more than 10 copies per bacterial cell, and a viral expression cassette comprising a cDNA of said polynucleotide and comprising cis-regulatory elements for transcription of said viral cDNA in mammalian cells and for processing of the transcribed RNA into infectious RNA virus.

18. The polynucleotide according to any one of statements 1 to 17 wherein said T cell antigen is selected from the group consisting of the core antigen of HBC, OVA and EBNA1.

19. The polynucleotide according to any one of statements 1 to 18, wherein the encoded T cell antigen comprises the amino acid sequence of SEQ ID NO:3, or a fragment thereof comprising a T cell epitope.

20. The polynucleotide according to any one of statements 1 to 18, wherein the encoded T cell antigen comprises the amino acid sequence of SEQ ID NO:7 or a fragment thereof comprising a T cell epitope.

21. The polynucleotide according to any one of statements 1 to 18, wherein the encoded T cell antigen comprises the amino acid sequence of SEQ ID NO:10 or a fragment thereof comprising a T cell epitope.

22. The polynucleotide according to any one of statements 1 to 18, wherein the encoded T cell antigen compromises the amino acid sequence of SEQ ID NO:13.

23. A flavivirus fusion construct characterized in that the flavivirus is preceded at its aminoterminus by:

a part of a flavivirus Capsid protein comprising or consisting of the N terminal part of the flavivirus Capsid protein, an immunogenic protein, or a part thereof comprising an immunogenic peptide, and a 2A cleaving peptide.

For the purpose of vaccination, these flavivirusses are typically life infectious attenuated viruses.

24. A flavivirus fusion construct to statement 23, wherein the part of the flavivirus Capsid protein comprises or consists of the 21 N terminal amino acids of the flavivirus Capsid protein.

25. The flavivirus fusion construct according to statement 23 or 24, wherein the flavivirus is yellow fever virus.

26. The flavivirus fusion construct statements 23, 24 or 25, where the terminal part of the Yellow Fever virus capsid consists of the sequence (SEQ ID NO: 2)

MSGRKAQGKTLGVNMVRRGVR.

27. The polynucleotide according to any one of statements 23 to 25, wherein the 2A cleaving peptide comprises the sequence DXEXNPGP [SEQ ID NO:46].

28. The flavivirus fusion construct according to any one of statements 23 to 26, wherein the 2A cleaving peptide comprises the sequence LxxxGDVExPGP [SEQ ID NO:17]

29. The flavivirus fusion construct according to any one of statements 23 to 28, wherein the 2A cleaving peptide comprises the sequence LLTCGDVEENPGP [SEQ ID NO:18].

30 The flavivirus fusion construct according to any one of statements 23 to 28, wherein the 2A cleaving peptide is the *Thosea asigna* 2A peptide with amino acid sequence EGRGSLLTCGDVEENPGP (SEQ ID NO:16).

31. The flavivirus fusion construct according to any one of statements 23 to 30, wherein the amino acid C terminal of the 2A cleaving peptide is Gly, Ala, Ser or Thr.

32. The flavivirus fusion construct polynucleotide according to any one of statements 23 to 31, wherein the immunogenic protein is a T cell antigen and the immunogenic fragment thereof comprises a T cell epitope.

33. The flavivirus fusion construct according to any one of statements 23 to 32, wherein the Yellow Fever virus is the YF 17D attenuated virus.

34. The flavivirus fusion construct according to any one of statements 23 to 32, wherein the immunogenic protein is selected from the group consisting of the core antigen of HBC, OVA and EBNA1.

35. The flavivirus fusion construct according to any one of statements 23 to 32, wherein the HBC antigen comprises the amino acid sequence of SEQ ID NO:7, or a fragment thereof comprising a T cell epitope.

36. The polynucleotide according to any one of statements 1 to 22, for use as a vaccine.

37. The polynucleotide for use as a vaccine according to statement 36, in the prevention of an infection caused by said immunogenic protein or immunogenic peptide fragment thereof.

38. The polynucleotide for use as a vaccine according to statement 36, in the simultaneous prevention of an infection caused by said immunogenic protein or immunogenic peptide fragment thereof and of a flavivirus infection.

39. The flavivirus fusion construct according to any one of statements 23 to 35, for use as a vaccine.

40. The flavivirus fusion construct for use as a vaccine according to statement 39, in the prevention of an infection caused by said immunogenic protein or immunogenic peptide fragment thereof.

41. The flavivirus fusion construct for use as a vaccine according to statement 40, the simultaneous prevention of an infection caused by said immunogenic protein or immunogenic peptide fragment thereof and of a flavivirus infection.

42. The flavivirus fusion construct for use as a vaccine according to statement 40, in the simultaneous prevention of an infection caused by said T cell antigen or partial T cell epitope and of a Yellow Fever infection.

43. A pharmaceutical comprising a polynucleotide in accordance with any one of statements 1 to 22, and a pharmaceutical acceptable carrier.

44. A pharmaceutical comprising a flavivirus fusion construct in accordance with any one of statements 23 to 35, and a pharmaceutical acceptable carrier.

45. A method of preparing a vaccine against a immunogenic protein or peptide fragment thereof, comprising the steps of:

(a) providing a BAC which comprises an inducible bacterial ori sequence for amplification of said BAC to more than 10 copies per bacterial cell, and a viral expression cassette comprising a cDNA of a polynucleotide according to any one of statements 1 to 22, and comprising cis-regulatory elements for transcription of said cDNA in mammalian cells and for processing of the transcribed RNA into infectious RNA virus (b) transfecting mammalian cells with the BAC of step (a)

(c) validating replicated virus of the transfected cells of step (b) for virulence and the capacity of generating antibodies against said T cell antigen, cloning the virus validated in step (c) into a vector, formulating the vector into a vaccine formulation.

46. The method according to statement 45, wherein the vector is a BAC, which comprises an inducible bacterial ori sequence for amplification of said BAC to more than 10 copies per bacterial cell.

47. A method of provoking an immune response to an immunogenic protein, comprising the step of administering an effective amount of a polynucleotide in accordance with any one of statements 1 to 22, or a flavivirus fusion construct in accordance with any one of statements 23 to 35.

DETAILED DESCRIPTION

FIG. 1: Detail of polyprotein of YFV 17D/HBc. The first 155 amino acids of HBc, serotype ayw are preceded upstream of the YFV 17D capsid (amino acids 1-21) and followed downstream by the *Thosea asigna* 2A peptide and the full-length YFV 17D polyprotein, including the capsid protein.

Figure 2:
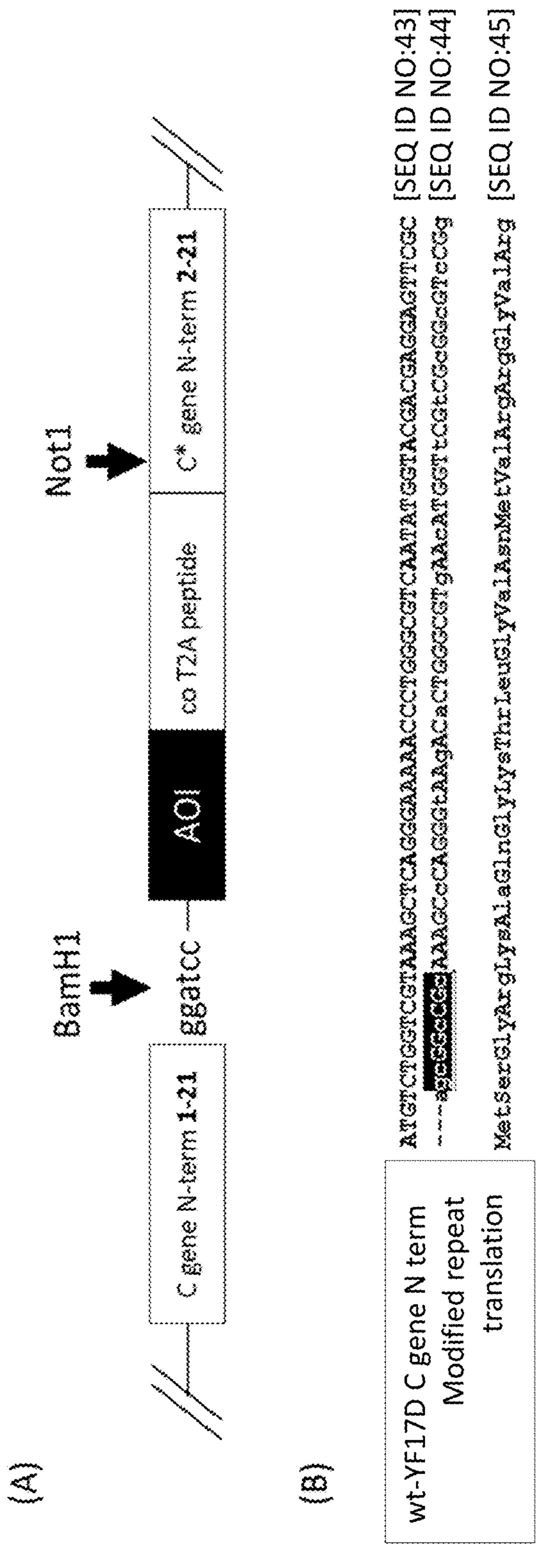

FIG. 2: shows a schematic map of cDNA constructs of the present invention. The Antigen Of Interest (AOI; e.g. HBV core antigen) is inserted as translational fusion to the first 21 N-terminal codons of the C gene in the YFV 17D ORF (C gene N-term 1-21) following an newly introduced in-frame BamH1 restriction endonuclease site. The AOI is fused C-terminally to a codon-optimized *Thosea asigna* virus 2A 'cleaving' peptide (co T2A peptide) followed by a codon modified repeat of the 2-21 codons of the YFV 17D C-gene (C* gene N-term 2-21). Downstream of latter cDNA element the construct continues as genuine YFV 17D cDNA.

Sequence alignment of first 21 codons of the wild-type YFV 17D ORF (wt-YF 17D C gene N-term) with the modified repeat thereof (Modified repeat) encoding for C* gene N-term 2-21 in (A). Small letters indicate nucleotide changes introduced relative to wt-YF 17D C gene N-term. A newly introduced Not1 restriction endonuclease site (gcGGcCGc) is highlighted in Black.

Figure 3:
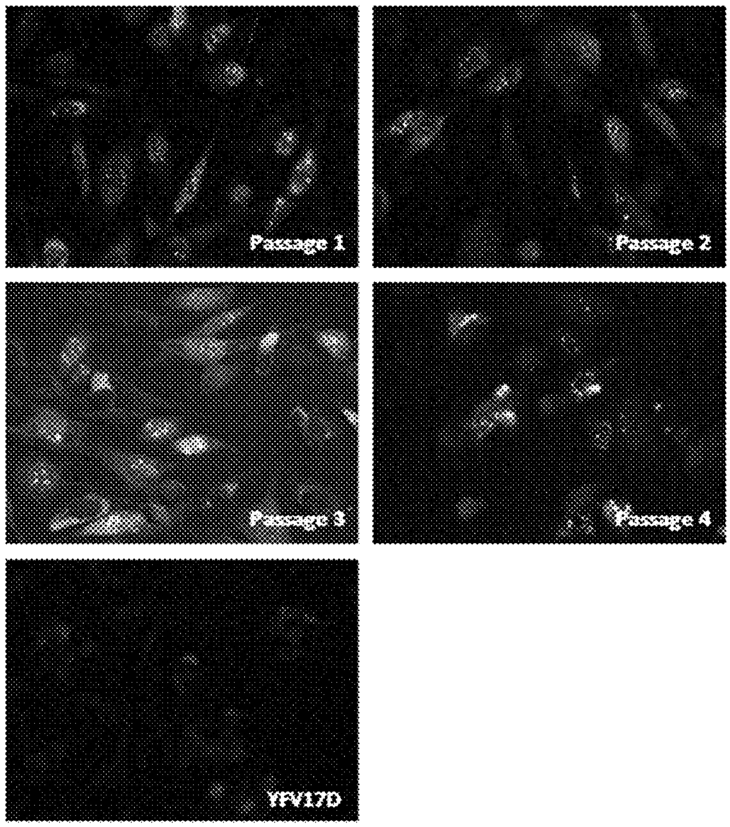

FIG. 3: Immunofluorescence imaging of YFV 17D/HBc passages and YFV 17D. Red: HBc, Green: YFV antigens.

Figure 4:
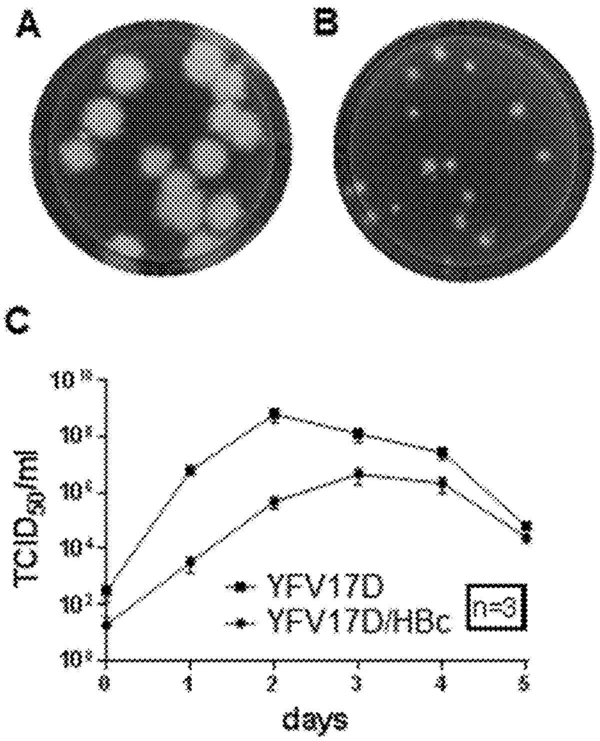

FIG. 4: in vitro characterization of YFV 17D/HBc. A) YFV 17D plaques, B) YFV 17D/HBc, C) growth curves of YFV 17D and YFV 17D/HBc.

Figure 5:
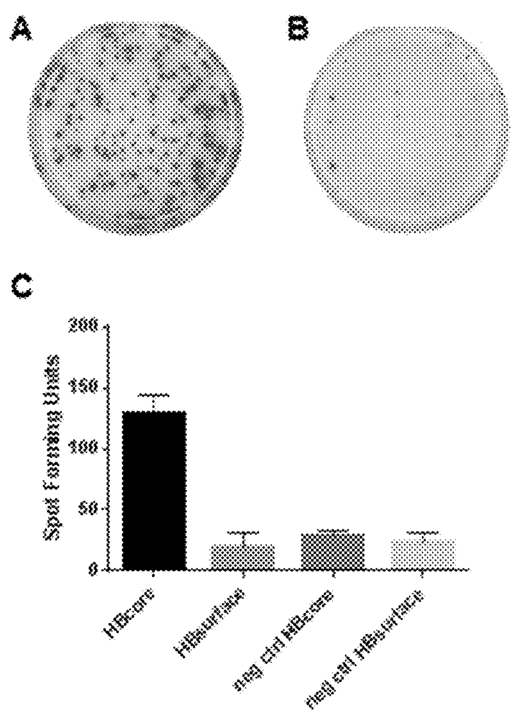

FIG. 5: mouse IFN-γ ELISPOT. Splenocytes isolated from YFV 17D/HBc-immunized AG129 mice were stimulated with peptides derived from HBcAg (A) and HBsAg (B). Spot forming units (SFU) for splenocytes of YFV 17D/HBc and Chimerivax-JE immunized mice stimulated with HBcAg and HBsAg (C).

Figure 6:
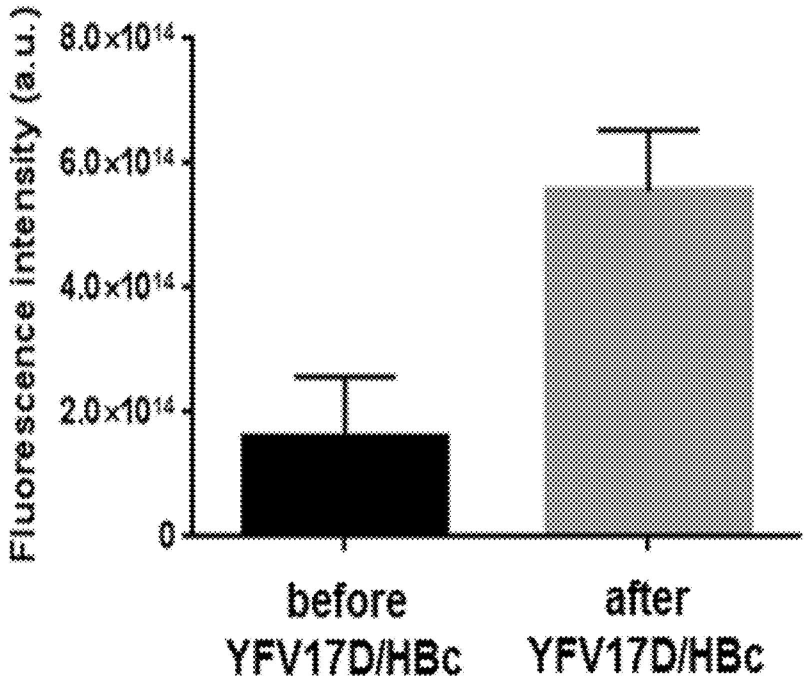

FIG. 6: Fluorescence intensities from immunofluorescence assay with serum collected before and after YFV 17D/HBc immunization.

Figure 7:
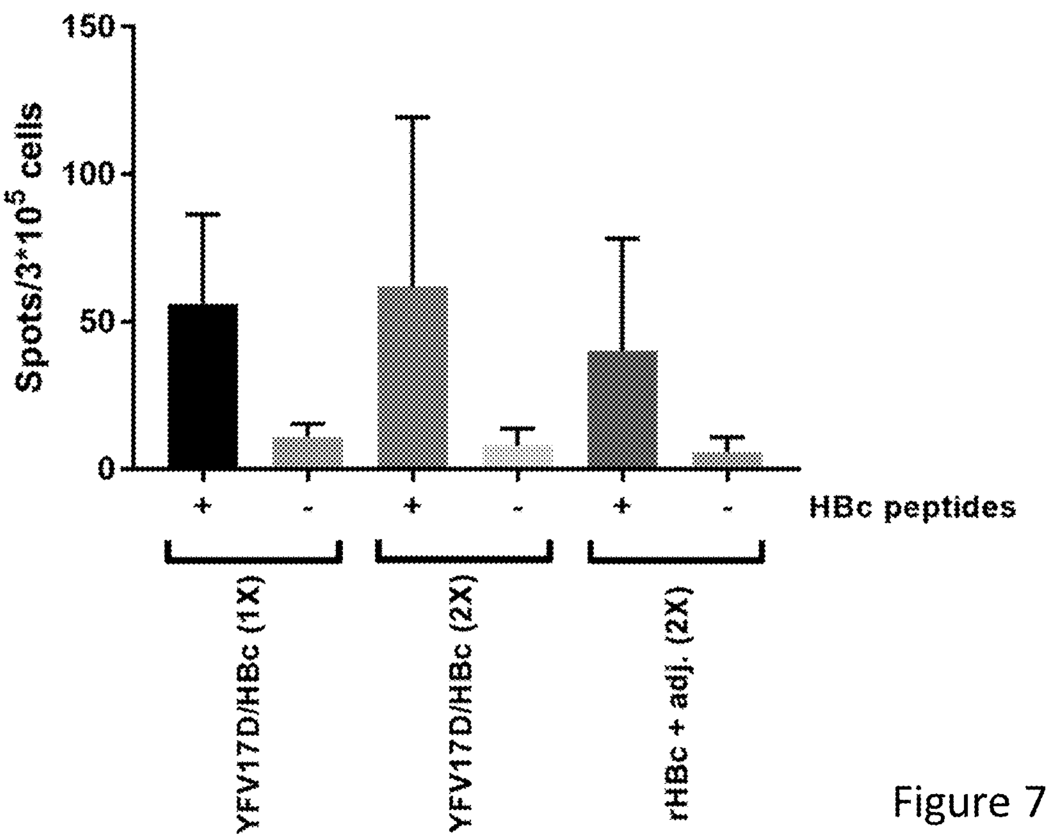

FIG. 7: mouse IFN-γ ELISPOT. SFU for splenocytes ($3\times10^5$) isolated from AG129 mice immunized once (1×) or twice (2×) with YFV 17D/HBc or twice with rHBc+Quil-A®, stimulated with peptides derived from HBcAg (+) or not stimulated (−).

Figure 8:
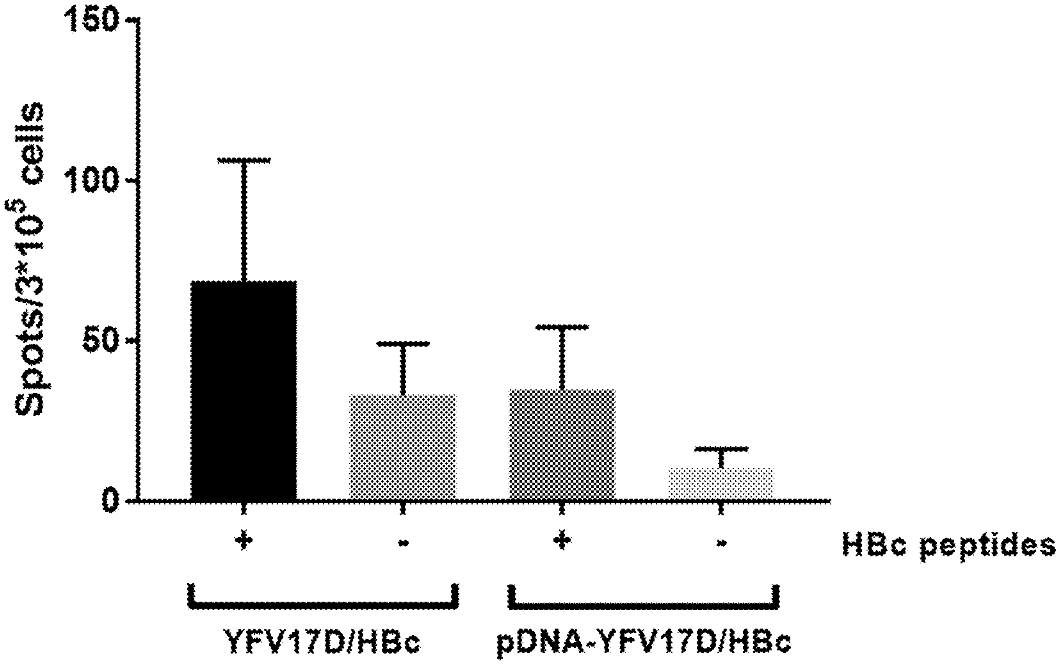
Figure 8:
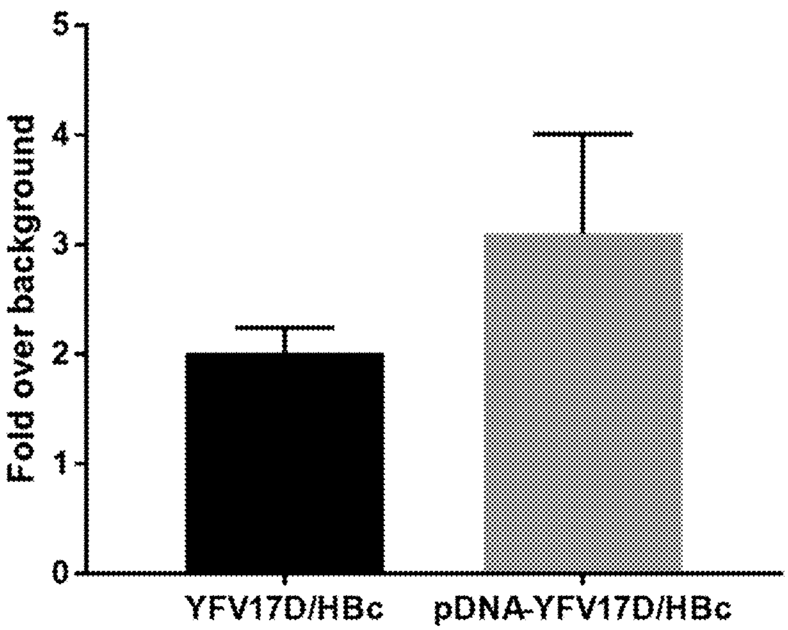

FIG. 8: mouse IFN-γ ELISPOT. A) SFU for splenocytes ($3\times10^5$) isolated from AG129 mice immunized with YFV 17D/HBc or with pDNA-YFV 17D/HBc and PEI, stimulated with peptides derived from HBcAg (+) or not stimulated (−). B) fold over background (HBc peptide-stimulated over non-stimulated) for splenocytes isolated from AG129 mice immunized with YFV 17D/HBc or with pDNA-YFV 17D/HBc and PEI.

Figure 9:
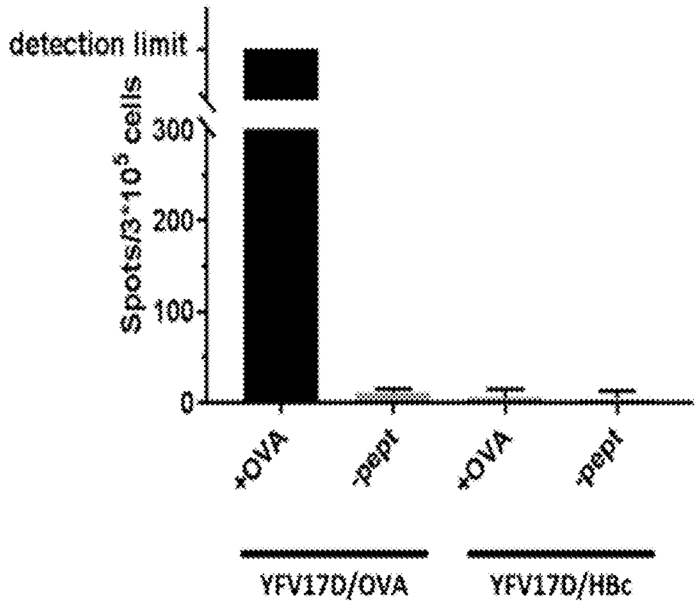
Figure 9:
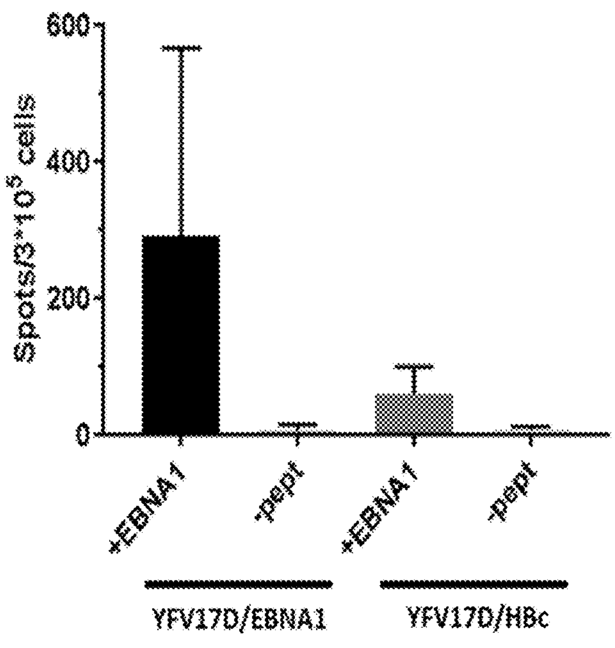

FIG. 9: mouse IFN-γ ELISPOT. A) SFU for splenocytes ($3\times10^5$) isolated from AG129 mice immunized with YFV 17D/OVA (and YFV 17D/HBc as negative control), stimulated with a peptide derived from chicken ovalbumin (+OVA) or not stimulated (−pept). B) SFU for splenocytes ($3\times10^5$) isolated from AG129 mice immunized with YFV 17D/EBNA1 (and YFV 17D/HBc as negative control), stimulated with a peptide mixture derived from EBNA1 (+EBNA1) or not stimulated (−pept).

The present invention overcomes the prior art problems using one or more of the following modifications.

A more efficient cleaving peptide has been used namely *Thosea asigna* virus 2A peptide (T2A) [Donnelly et al. (2001) *J Gen Virol* 82, 1027-1041], the use of this peptide also overcomes the need to include a further ubiquitin cleavage sequence. Apart from *Thosea asigna*, other viral 2A peptides can be used in the compounds and methods of the present invention. Examples hereof are described in e.g. Chng et al. (2015) *MAbs* 7, 403-412, namely APVKQTLNFDLLKLAGDVESNPGP of foot-and mouth disease virus [SEQ ID NO: 38], ATNFSLLKQAGDVEENPGP [SEQ ID NO: 39] of porcine teschovirus-1, and QCTNYALLKLAGDVESNPGP from equine rhinitis A virus [SEQ ID NO: 40]. These peptides have a conserved LxxxGDVExNPGP motif [SEQ ID NO: 17]. Peptides with this consensus sequence can be used in the compounds of the present invention. Other suitable examples of viral 2A cleavage peptides represented by the consensus sequence DXEXNPGP [SEQ ID NO:46] are disclosed in Souza-Moreira et al. (2018) *FEMS Yeast Res*. August 1. Further suitable examples of 2A cleavage peptides from as well picornaviruses as from insect viruses, type C rotaviruses, trypanosome and bacteria (*T. maritima*) are disclosed in Donnelly (2001) *J Gen Virol.* 82, 1027-1041.

The present invention is illustrated with a yellow fever but can be equally performed using other flavivirus based constructs such as but not limited to, Japanese Encephalitis, Dengue, Murray Valley Encephalitis (MVE), St. Louis Encephalitis (SLE), West Nile (WN), Tick-borne Encephalitis (TBE), Russian Spring-Summer Encephalitis (RSSE), Kunjin virus, Powassan virus, Kyasanur Forest Disease virus, Zika virus, Usutu virus, Wesselsbron and Omsk Hemorrhagic Fever virus.

The viral fusion constructs further contains a repeat of the N-terminal part of the Capsid protein. In the present invention the repeat has the same amino acid sequence but the DNA sequence has been modified to include synonymous codons, resulting in a maximally ~75% nucleotide sequence identity over the 21 codons used [herein codon 1 is the start ATG]. As demonstrated by Samsa et al. (2012) J. Virol. 2012 86,1046-1058 the Capsid N-terminal part may be not limited to the 21 AA Capsid N terminal part, and may comprise for example an additional 5, 10, 15, 20 or 25 amino acids. Prior art only mutated cis-acting RNA structural elements from the repeat [Stoyanov (2010) *Vaccine* 28, 4644-4652]. The approach of the present invention thus also abolishes any possibility for homologous recombination, which leads to an extraordinary stable viral fusion construct.

In typical embodiment the nucleotide sequence encoding the N-terminal part of the capsid protein, which is located 5' of the sequence encoding the epitope or antigen is identical to the sequence of the virus used for the generation of the construct. The mutations which are introduced to avoid recombination are introduced in the nucleotide sequence encoding the N-terminal part of the capsid protein, which is located 3' of the sequence encoding the epitope or antigen.

Furthermore in the repeat of the C gene encoding the Capsid, the sequence only starts from the second codon, which likely affects cleavage from T2A; T2A cleavage is favored in the constructs of the present invention because the amino acid (aa) c terminal of the T2A 'cleavage' site (NPG/P) [SEQ ID NO: 47] is a small aa, namely serine (NPG/PS) [SEQ ID NO: 48] or alternatively Gly, Ala, or Thr instead of the start methionine in the original Capsid protein.

Further also codon-optimized cDNAs are used for the antigens that are cloned flavivirus constructs.

Overall, one or more of the above modifications minimize the replicative burden of inserting extra 'cargo' in the vector that would otherwise unavoidably pose on a fitness cost on YFV replication.

The present invention is illustrated with immunogenic proteins comprising T cell epitopes but is applicable to any immunogenic protein which induce an humoral and/or cell-mediated immune response and include proteins comprising e.g. B cell epitopes or NKT epitopes. Immunogenic proteins can be for example human proteins causing autoimmune diseases or tumor antigens, and animal, plant, bacterial, fungal, or viral antigens causing allergies or infections.

The present invention relates to the use for vaccination purposes of (i) the plasmid DNA molecule encoding a full-length recombinant YFV 17D genome containing the coding sequence of the HBcAg, (ii) the infectious RNA molecule that is encoded on said plasmid DNA and (iii) the recombinant live-attenuated virus obtained from cell cultures transfected with said plasmid DNA. The invention also comprises (i) the preparation of the plasmid DNA in bacteria or yeast and (ii) the preparation of the recombinant live-attenuated virus from in vitro cell cultures or rodent tissues.

Described herein is the plasmid DNA molecule encoding a full-length recombinant live-attenuated yellow fever virus genome and derivatives thereof for vaccination purposes. Recombinant live-attenuated virus obtained by transfection of said plasmid DNA in in vitro cell cultures expresses hepatitis B virus core antigen and generates both a humoral and cellular immune response in mice lacking both interferon type I and type II receptors.

The propagation of the chimeric constructs prior to attenuation, as well as the cDNA of a construct after attenuation requires an error proof replication of the construct. The use of Bacterial Artificial Chromosomes, and especially the use of inducible BACS as disclosed by the present inventors in WO2014174078, is particularly suitable for high yield, high quality amplification of cDNA of RNA viruses such as chimeric constructs of the present invention.

A BAC as described in this publication BAC comprises:

an inducible bacterial ori sequence for amplification of said BAC to more than 10 copies per bacterial cell, and a viral expression cassette comprising a cDNA of an the RNA virus genome and comprising cis-regulatory elements for transcription of said viral cDNA in mammalian cells and for processing of the transcribed RNA into infectious RNA virus.

As is the case in the present invention the RNA virus genome is a chimeric viral cDNA construct of two virus genomes.

In these BACS, the viral expression cassette comprises a cDNA of a positive-strand RNA virus genome, an typically a RNA polymerase driven promoter preceding the 5' end of said cDNA for initiating the transcription of said cDNA, and an element for RNA self-cleaving following the 3' end of said cDNA for cleaving the RNA transcript of said viral cDNA at a set position.

The BAC may further comprise a yeast autonomously replicating sequence for shuttling to and maintaining said bacterial artificial chromosome in yeast. An example of a yeast ori sequence is the 2μ plasmid origin or the ARS1 (autonomously replicating sequence 1) or functionally homologous derivatives thereof.

The RNA polymerase driven promoter of this first aspect of the invention can be an RNA polymerase II promoter, such as Cytomegalovirus Immediate Early (CMV-IE) promoter, or the Simian virus 40 promoter or functionally homologous derivatives thereof.

The RNA polymerase driven promoter can equally be an RNA polymerase I or III promoter.

The BAC may also comprise an element for RNA self-cleaving such as the cDNA of the genomic ribozyme of hepatitis delta virus or functionally homologous RNA elements.

The formulation of DNA into a vaccine preparation is known in the art and is described in detail in for example chapter 6 to 10 of "DNA Vaccines" Methods in Molecular Medicine Vol 127, (2006) Springer Saltzman, Shen and Brandsma (Eds.) Humana Press. Totoma, N.J. and in chapter 61 Alternative vaccine delivery methods, Pages 1200-1231, of Vaccines (6th Edition) (2013) (Plotkin et al. Eds.). Details on acceptable carrier, diluents, excipient and adjuvant suitable in the preparation of DNA vaccines can also be found in WO2005042014, as indicated below.

"Acceptable carrier, diluent or excipient" refers to an additional substance that is acceptable for use in human and/or veterinary medicine, with particular regard to immunotherapy.

By way of example, an acceptable carrier, diluent or excipient may be a solid or liquid filler, diluent or encapsulating substance that may be safely used in systemic or topic administration. Depending upon the particular route of administration, a variety of carriers, well known in the art may be used. These carriers may be selected from a group including sugars, starches, cellulose and its derivatives, malt, gelatine, talc, calcium sulphate and carbonates, vegetable oils, synthetic oils, polyols, alginic acid, phosphate buffered solutions, emulsifiers, isotonic saline and salts such as mineral acid salts including hydrochlorides, bromides and sulphates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, (1991)) which is incorporated herein by reference.

Any safe route of administration may be employed for providing a patient with the DNA vaccine. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intramuscular and subcutaneous injection may be appropriate, for example, for administration of immunotherapeutic compositions, proteinaceous vaccines and nucleic acid vaccines.

It is also contemplated that microparticle bombardment or electroporation may be particularly useful for delivery of nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

DNA vaccines suitable for oral or parenteral administration may be presented as discrete units such as capsules, sachets or tablets each containing a pre-determined amount of plasmid DNA, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the DNA plasmids with liquid carriers or finely divided solid carriers or both, and then, if necessary, shaping the product into the desired presentation.

The above compositions may be administered in a manner compatible with the dosage formulation, and in such amount as is effective. The dose administered to a patient, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

Furthermore DNA vaccine may be delivered by bacterial transduction as using live-attenuated strain of *Salmonella* transformed with said DNA plasmids as exemplified by Darji et al. (2000) FEMS Immunol. Med. Microbiol. 27, 341-349 and Cicin-Sain et al. (2003) J. Virol. 77, 8249-8255 given as reference.

Typically the DNA vaccines are used for prophylactic or therapeutic immunisation of humans, but can for certain viruses also be applied on vertebrate animals (typically mammals, birds and fish) including domestic animals such as livestock and companion animals. The vaccination is envisaged of animals which are a live reservoir of viruses (zoonosis) such as monkeys, mice, rats, birds and bats.

In certain embodiments vaccines may include an adjuvant, i.e. one or more substances that enhances the immunogenicity and/or efficacy of a vaccine composition However, life vaccines may eventually be harmed by adjuvants that may stimulate innate immune response independent of viral replication. Non-limiting examples of suitable adjuvants include squalane and squalene (or other oils of animal origin); block copolymers; detergents such as Tween-80; Quill A, mineral oils such as Drakeol or Marcol, vegetable oils such as peanut oil; *Corynebacterium*-derived adjuvants such as *Corynebacterium parvum; Propionibacterium*-derived adjuvants such as *Propionibacterium acne; Mycobacterium bovis* (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOMt) and ISCOMATRIX (B) adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

Example 1. Materials and Methods

Indirect immunofluorescence assay: For detection of HBcAg expressed from YFV-HBc, baby hamster kidney cells strain 21J (BHK21J) were transfected with PLLAV-YFV-HBc. Per chamber of an 8-chamber slide (Milliwell® EZ slide, Millipore) 50,000 BHK21J cells were seeded and transfected the following day with a mixture of 100 ng PLLAV-YFV-HBc in 9 µl serum-free medium and 0.3 µl TransIT®-LT1 transfection reagent (Mirus® Bio LLC, US). Cells were fixed two days later with 3.7% formaldehyde in PBS, permeabilized with 0.1% Triton X-100 in PBS and subsequently incubated with a polyclonal mouse antibody raised against YFV antigens and a polyclonal rabbit antibody raised against HBcAg at a dilution of 1:500. The YFV antigens and HBcAg were detected with an Alexa Fluor®488-conjugated goat anti-mouse IgG and an Alexa Fluor®647-conjugated donkey anti-rabbit IgG, respectively. Plaque assay: For the visualization of virus plaques, $5\times10^5$ BHK21J cells were used to seed each well of a 12-well polystyrene microplate (Falcon, Corning). The following day these monolayers were incubated with 1 ml of a serial dilution of the virus for 1 hour and subsequently overlayed with a 1:1 mixture of 1% LMP agarose in $dH_2O$ and MEM 2× medium. After 5 days of incubation time at 37° C. and 5% $CO_2$, cells were fixed with 8% formaldehyde in PBS. After removal of the agarose overlay plaques were visualized by staining of the cells with 1% methylene blue in PBS and 10% ethanol.

ELISPOT: To assess whether the YFV-HBc could stimulate splenocytes of immunized mice to secrete IFN-γ, an enzyme-linked immunospot (ELISPOT) assay was performed (mouse IFN gamma ELISPOT Ready-SET-Go!®, eBioscience), according to the manufacturer's protocol. Briefly, polyvinylidene difluoride-backed ninety-six-well plates (Millipore) were coated with an IFN-γ-binding capture antibody and stored overnight at 4° C. Splenocytes were added at a density of $4\times10^5$ cells per well in triplicate. Peptide (5 µg/ml) was used to stimulate the cells. The plates were incubated for 24 hours at 37° C. and 5% $CO_2$. Plates were washed and a biotinylated detection antibody was added. After 2 hours, avidin-HRP was added to the wells and incubated again for 45 minutes before the addition of the substrate AEC, 3-amino-9-ethylcarbazole. The colorimetric reaction was stopped after 10 minutes by washing the plate with $dH_2O$. Spots were counted with an AID ELISPOT reader (Autoimmun Diagnostika GmbH, Germany).

Example 2. Construction and In Vitro Characterization of Recombinant Yellow Fever 17D Virus The construction of a HBc-expressing YFV 17D (YFV 17D/HBc) was based on a patented reverse genetics system that comprises a full-length YFV 17D cDNA as an expression cassette on a bacterial artificial chromosome (BAC) [Dallmeier & Neyts, WO2014/174078A1], henceforth called pShuttle/YFV 17D.WO2014174078A1 The viral cDNA was modified to encode the hepatitis B virus core antigen (HBcAg), serotype ayw, nucleotides 1-465. This sequence was inserted in frame into the YFV 17D cDNA, preceded upstream by 63 nucleotides encoding the first 21 amino acids of the YFV 17D capsid protein, and was followed immediately downstream by a 2A peptide of *Thosea asigna* virus to ensure post-translational cleavage from the YFV 17D polypeptide, and by the rest of the viral polyprotein (including the full-length capsid gene, nucleotides 2-10862) [[Stoyanov (2010) *Vaccine* 28, 4644-4652]. To prevent recombination between the two sequences coding for YFV 17D capsid upstream and downstream of HBc, synonymous codons were used (FIG. 1). This BAC expressing the YFV 17D/HBc will henceforth be referred to as pShuttle/YFV 17D/HBc. For the construction of pShuttle/YFV 17D/HBc, following cloning steps were performed (schematic map in FIG. 2). First, we inserted an URA3 gene expression cassette upstream of the YFV 17D capsid gene, flanked by a TEF promoter and a TEF terminator, upstream and downstream of the URA3 gene, respectively. The rationale behind this is to create a vector which offers increased ease of cloning, by introducing the selection marker URA3 (enabling counter-selection with 5-fluoroorotic acid (5-FOA)). This cassette was preceded upstream by 63 nucleotides encoding the first 21 amino acids of the YFV 17D capsid protein and was followed immediately downstream by a 2A peptide of *Thosea asigna* virus (T2A peptide) and the rest of the viral polyprotein. A custom synthesized DNA fragment (gBlock, Integrated DNA Technologies, Leuven, Belgium) encoding this expression cassette was amplified by PCR with primers #3 and #4 (see Table 1 for all primer sequences), and the resulting PCR product was further elongated in subsequent PCRs with primer pairs #5 & #6, #7 & #15 and #15 & #17. The destination plasmid, encoding red fluorescent protein mCherry from the same site in the YFV 17D capsid gene (pShuttle/YFV 17D/mCherry), was digested with restriction enzyme NotI at a unique site in the plasmid. Both PCR product and restricted destination plasmid (with overlapping ends) were transformed into yeast cells (*S. cerevisiae*, strain YPH500), and recombined in these cells by homologous recombination of the overlapping ends, into pShuttle/YFV 17D/URA3. Second, we used the two PmeI sites flanking the URA3 gene to excise URA3 back out of pShuttle/YFV 17D/URA3, and transformed this open vector back into yeast, together with a PCR-amplified gBlock encoding the first 155 amino acids of HBc (amplified and elongated in subsequent PCRs with primer pairs #8 & #16, #5 & #6, #15 & #7 and #15 & #17) [or encoding the first 155 amino acids of HBc, followed by the coding sequence of green fluorescent protein LOV [Buckley (2015) *Curr. opinion chem. biol.* 27, 39-45] (amplified and elongated in subsequent PCRs with primer pairs #8 & #9, #5 & #6, #15 & #7 and #15 & #17)]. By homologous recombination of the overlapping ends of PCR product and digested vector in yeast, this resulted in pShuttle/YFV 17D/HBc.

Viability and transgene expression of YFV 17D/HBc was assessed by transfection of pDNA-YFV 17D/HBc into BHK21J cells. Immunofluorescence staining revealed stable expression of HBc in addition to YFV 17D antigens. To determine if the resulting virus YFV 17D/HBc stably expressed the transgene, it was passaged consecutively once every 3 days. Immunofluorescence staining showed stable expression of intact HBc up to passage 4 (FIG. 3).

The supernatant after transfection of pDNA-YFV 17D/HBc was used in a plaque assay to investigate whether infectious virus was produced, and compared side by side with the parental YFV 17D. Five days post-infection, the plaques produced by the recombinant YFV 17D/HBc were visibly smaller than those produced by YFV 17D (FIGS. 4A and 4B). Kinetics of viral replication was investigated by generation of a growth curve of YFV 17D/HBc and YFV 17D by infection of BHK21J cells (MOI 0.01) and titration of supernatant collected over the course of five days (FIG. 4C).

Example 3. Cellular Immune Response in Mice Immunized with YFV 17D/HBc

To determine if YFV 17D/HBc could prime an immune response in vivo, three AG129 mice (lacking both type I and type II interferon (IFN) receptors) were immunized i.p. with $4.5\times10^4$ plaque forming units (PFU) and boosted with $4.5\times10^4$ PFU after two weeks. As AG129 generally do not survive an injection with YFV 17D, a single injection ($9\times10^4$ PFU) of a chimeric YFV/Japanese encephalitis virus vaccine strain (Chimerivax-JE) was used as negative control (2 mice). To detect levels of HBc-specific IFN-γ secretion by peptide-stimulated T-cells, the mice were sacrificed seven weeks after the first injection and their splenocytes used in a mouse IFN-γ enzyme-linked immunospot assay (ELISPOT). Splenocytes were stimulated with peptides derived from either HBcAg or HBsAg. Spot counts were distinctly higher when splenocytes from YFV 17D/HBc-immunized mice were stimulated with HBcAg-derived peptides compared to stimulation with HBsAg-derived peptides, or stimulation of splenocytes from the negative control group with either peptide (FIGS. 5A and 5B).

Example 4. Humoral Immune Response in Mice Immunized with YFV 17D/HBc

To investigate whether immunization with YFV 17D/HBc could mount an antibody response against the HBc transgene, three AG129 mice were immunized i.p. with $7.5\times10^4$ PFU YFV 17D/HBc and boosted five weeks later ($4.5\times10^4$ PFU). Before the first injection and three weeks after the booster, serum was collected and used in an immunofluorescence assay on HBV-infected human hepatoma cells. The use of serum collected after immunization resulted in a marked increase in fluorescence intensity compared to the use of preserum (FIG. 6).

Example 5. Homologous Prime-Boost of YFV 17D/HBc

To determine the significance of delivering a homologous booster dose of YFV 17D/HBc to HBc-specific T cell levels, mice were vaccinated once or twice (two weeks after the first dose) with $10^4$ pfu of YFV 17D/HBc. Splenocytes were harvested four weeks after the first dose of YFV 17D/HBc and stimulated with HBc-derived peptides in a mouse IFNγ ELISPOT assay. Spot counts for YFV 17D/HBc double-vaccinated mice were not significantly higher than those of single-vaccinated mice. Two shots of 10 μg recombinant HBc (rHBc, American Research Products Inc, Waltham, MA, USA) adjuvanted by 10 μg of Quil-A® (InvivoGen, San Diego, CA, USA) did not elicit higher levels of IFNγ-secreting T cells than our vaccine candidate (FIG. 7).

Example 6. Mounting of HBc-Specific T Cell Responses by Vaccination with pDNA-YFV 17D/HBc As mentioned above, transfection of YFV 17D/HBc-encoding plasmid DNA (pDNA-YFV 17D/HBc) in BHK21J results in release of infectious virus (YFV 17D/HBc) in the cell culture supernatant, which can be used directly to inoculate mice. We have administered pDNA-YFV 17D/HBc to AG129 mice as such, by two intraperitoneal injections of a mixture of this plasmid (3 μg) and in vivo transfection reagent polyethylene imine (PEI), separated by one week. Two weeks after the first injection, mice were sacrificed and their splenocytes used in a mouse IFNγ ELISPOT assay, which showed that HBc-specific T cells had been elicited by pDNA-YFV 17D/HBc (FIG. 8).

Example 7. Mounting of Specific T Cell Responses Against Other Antigens Expressed from the Capsid Gene of YFV 17D Other T cell antigens were cloned into the site of the YFV 17D capsid gene, as described above, namely the full-length chicken ovalbumin (OVA) and the full-length Epstein-Barr virus nuclear antigen 1 (EBNA1).

The OVA insert was amplified by PCR from a gBlock (Integrated DNA Technologies, Leuven, Belgium) which contained the coding sequence of the full-length chicken ovalbumin, flanked on its 5' end by the coding sequence of the first 21 amino acids of the YFV 17D capsid protein, and on its 3' end by the coding sequence of the T2A peptide, with primers #1 and #2 (see Table 1 for all primer sequences), and elongated by subsequent PCRs with primer pairs #5 & #7, and #15 & #17. Then, pShuttle/YFV 17D/OVA was made by homologous recombination in yeast of the PCR insert and PmeI-restricted pShuttle/YFV 17D/URA3 destination plasmid, as described for pShuttle/YFV 17D/HBc.

The EBNA1 insert was amplified by PCR from a plasmid which contained the coding sequence of the full-length EBNA1 (kindly provided by professor Christian Münz, University of Zürich) with primers #9 and #10, and elongated by subsequent PCRs with primer pairs #5 & #6, and #15 & #17. Then, pShuttle/YFV 17D/EBNA1 was made by homologous recombination in yeast of the PCR insert and PmeI-restricted pShuttle/YFV 17D/URA3 destination plasmid, as described for pShuttle/YFV 17D/HBc. Both pShuttle/YFV 17D/OVA and pShuttle/YFV 17D/EBNA1 were transfected in BHK21J, as described for pShuttle/YFV 17D/HBc, resulting in the release of infectious virus in the supernatant, henceforth called YFV 17D/OVA and YFV 17D/EBNA1, respectively.

To investigate the T cell responses elicited by YFV 17D/OVA and YFV 17D/EBNA1 in vivo, three AG129 mice were immunized once i.p. with $1\times10^6$ $TCID_{50}$ of YFV 17D/OVA and three AG129 mice were immunized once i.p. with $1\times10^6$ $TCID_{50}$ of YFV 17D/EBNA1. A single injection ($1\times10^6$ $TCID_{50}$) of YFV 17D/HBc was used as negative control (3 AG129 mice). To detect levels of HBc-specific IFN-γ secretion by peptide-stimulated T-cells, the mice were sacrificed five weeks later and their splenocytes were used in a mouse IFNγ ELISPOT. For the mice vaccinated with YFV 17D/OVA, splenocytes were stimulated with 5 μg of mixture of peptides derived from EBNA1 (kindly provided by professor Christian Münz, University of Zürich). Both YFV 17D/OVA and YFV 17D/EBNA1 elicited strong and specific IFNγ responses to peptides of ovalbumin and EBNA1, respectively (FIG. 9).

TABLE 1

| Primer sequences | | |
|---|---|---|
| Primer | Sequence (5' to 3') | SEQ ID NO: |
| #1 | aagctcaggg aaaaaccctg ggcgtcaata tggtacgacg aggagttcgc ggatcc | 19 |
| #2 | gtgtcttacc ctgggctttg cggccgctag gaccggggtt ctcctccacg tcgccacagg | 20 |
| #3 | gtcaatatgg tacgacgagg agttcgcgga tccgtttaaa cctcgtcccc gccgggtcac | 21 |
| #4 | gtcgccacag gtcagcaggg acccgcgtcc ctcgtttaaa cagtatagcg accagcattc | 22 |
| #5 | cagaacatgt ctggtcgtaa agctcaggga aaaaccctgg gcgtcaatat ggtacgacga | 23 |
| #6 | accctgggct ttgcggccgc taggaccggg gttctcctcc acgtcgccac aggtcagcag | 24 |
| #7 | ccggacgccg cgacgaacca tcttcacgcc cagtgtctta ccctgggctt tgcggccgct | 25 |
| #8 | cctgggcgtc aatatggtac gacgaggagt tcgcggatcc atggacatcg acccttataa | 26 |
| #9 | cctccacgtc gccacaggtc agcagggacc cgcgtccctc cgcgagggcc tttccctcgg | 27 |
| #10 | gtcttaccct gggctttgcg gccgctagga ccggggttct cctccacgtc gccacaggtc | 28 |
| #11 | tggaggagaa ccccggtcct agcggccgca aagcccaggg taagacactg ggcgtgaaca | 29 |

TABLE 1-continued

| Primer sequences | | |
|---|---|---|
| #12 | taagacactg ggcgtgaaca tggttcgtcg cggcgtccgg tccttgtcaa acaaaataaa | 30 |
| #13 | tgacgcccag ggtttttccc tgagctttac gaccagacat gttctggtca gttctctgct | 31 |
| #14 | tcgatgtcca tggatccgcg aactcctcgt cgtaccatat tgacgcccag ggtttttccc | 32 |
| #15 | tcgattaatt ttaatcgttc gttgagcgat tagcagagaa ctgaccagaa catgtct | 33 |
| #16 | cctccacgtc gccacaggtc agcagggacc cgcgtccctc ggacctgcct cgtcgtc | 34 |
| #17 | tctttccaat ttgttttgtt ttttgtttta ttttgtttga caaggaccgg acgccgcgac | 35 |
| #18 | gggcgtcaat atggtacgac gaggagttcg cggatccatg ggtagaaggc catttttcca | 36 |
| #19 | cctccacgtc gccacaggtc agcagggacc cgcgtccctc ctcctgccct tcctcaccct | 37 |

Sequence of interest of pShuttle/YFV17D/URA3
Legend:

| | |
|---|---|
| UPPER CASE | YFV17D 5′-UTR |
| UNDERLINED UPPER CASE | coding sequence of first 21 amino acids of YFV17D capsid protein |
| Lower case italics | BamHI site |
| UPPER CASE ITALICS | TEF promotor and TEF terminator |
| BOLD UPPER CASE | URA3 gene |
| Underlined lower case | coding sequence of T2A (Thosea asigna 2A) peptide |
| Lower case | coding sequence of YFV17D genome, starting from amino acid #2 |

SEQ ID NO: 1
AGTAAATCCTGTGTGCTAATTGAGGTGCATTGGTCTGCAAATCGAGTTGCTAGGCAATAAACACATTTGG
ATTAATTTTAATCGTTCGTTGAGCGATTAGCAGAGAACTGACCAGAACATGTCTGGTCGTAAAGCTCAGG

SEQ ID NO: 2

M S G R K A Q
GAAAAACCCTGGGCGTCAATATGGTACGACGAGGAGTTCGC*ggatccGTTTAAACCTCGTCCCCGCCGGG*
G K T L G V N M V R R G V R
*TCACCCGGCCAGCGACATGGAGGCCCAGAATACCCTCCTTGACAGTCTTGACGTGCGCAGCTCAGGGGCA*
*TGATGTGACTGTCGCCCGTACATTTAGCCCATACATCCCCATGTATAATCATTTGCATCCATACATTTTG*
*ATGGCCGCACGGCGCGAAGCAAAAATTACGGCTCCTCGCTGCAGACCTGCGAGCAGGGAAACGCTCCCCT*
*CACAGACGCGTTGAATTGTCCCCACGCCGCGCCCCTGTAGAGAAATATAAAAGGTTAGGATTTGCCACTG*
*AGGTTCTTCTTTCATATACTTCCTTTTAAAATCTTGCTAGGATACAGTTCTCACATCACATCCGAACATA*
*AACAACC*ATGACAGTCAACACTAAGACCTATAGTGAGAGAGCAGAAACTCATGCCTCACCAGTAGCACAA
M T V N T K T Y S E R A E T H A S P V A Q SEQ ID NO: 3
CGATTATTTCGATTAATGGAACTGAAGAAAACCAATTTATGTGCATCAATTGATGTTGATACCACTAAGG
R L F R L M E L K K T N L C A S I D V D T T K E
AATTCCTTGAATTAATTGATAAATTGGGTCCTTATGTATGCTTAATCAAGACTCATATTGATATAATCAA
F L E L I D K L G P Y V C L I K T H I D I I N
TGATTTTTCCTATGAATCCACTATTGAACCATTATTAGAACTTTCACGTAAACATCAATTTATGATTTTT
D F S Y E S T I E P L L E L S R K H Q F M I F
GAAGATAGAAAATTTGCTGATATTGGTAATACCGTGAAGAAACAATATATTGGTGGAGTTTATAAAATTA
E D R K F A D I G N T V K K Q Y I G G V Y K I S
GTAGTTGGGCAGATATTACTAATGCTCATGGTGTCACTGGGAATGGAGTAGTTGAAGGATTAAAACAGGG
S W A D I T N A H G V T G N G V V E G L K Q G
AGCTAAAGAAACCACCACCAACCAAGAGCCAAGAGGGTTATTGATGTTAGCTGAATTATCATCAGTGGGA
A K E T T T N Q E P R G L L M L A E L S S V G
TCATTAGCATATGGAGAATATTCTCAAAAAACTGTTGAAATTGCTAAATCCGATAAGGAATTTGTTATTG
S L A Y G E Y S Q K T V E I A K S D K E F V I G
GATTTATTGCCCAACGTGATATGGGTGGACAAGAAGAAGGATTTGATTGGCTTATTATGACACCTGGAGT
F I A Q R D M G G Q E E G F D W L I M T P G V
TGGATTAGATGATAAAGGTGATGGATTAGGACAACAATATAGAACTGTTGATGAAGTTGTTAGCACTGGA
G L D D K G D G L G Q Q Y R T V D E V V S T G
ACTGATATTATCATTGTTGGTAGAGGATTGTTTGGTAAAGGAAGAGATCCAGATATTGAAGGTAAAAGGT
T D I I I V G R G L F G K G R D P D I E G K R Y
ATAGAGATGCTGGTTGGAATGCTTATTTGAAAAAGACTGGCCAATTATAA*TCAGTACTGACAATAAAAAG*
R D A G W N A Y L K K T G Q L *

TABLE 1-continued

Primer sequences

*ATTCTTGTTTTCAAGAACTTGTCATTTGTATAGTTTTTTTATATTGTAGTTGTTCTATTTTAATCAAATG*
*TTAGCGTGATTTATATTTTTTTTCGCCTCGACATCATCTGCCCAGATGCGAAGTTAAGTGCGCAGAAAGT*
*AATATCATGCGTCAATCGTATGTGAATGCTGGTCGCTATACTGTTTAAAC*gagggacgcgggtccctgct SEQ ID NO: 4
E G R G S L L
Gacctgtggcgacgtggaggagaaccccggtcctagcggccgcaaagcccagggtaagacactgggcgtg
T C G D V E E N P G P S G R K A Q G K T L G V
aacatggttcgtcgcggcgtccggtccttgtcaaacaaaataaaacaaaaaacaaaacaaattg
N M V R R G V R S L S N K I K Q K T K Q I Sequence of interest of pShuttle/YFV17D/HBc
Legend:

UPPER CASE YFV17D 5′-UTR
UNDERLINED UPPER CASE coding sequence of first 21 amino acids of YFV17D capsid protein
Lower case italics BamHI site
BOLD UPPER CASE HBc coding sequence
Underlined lower case coding sequence of T2A (Thosea asigna 2A) peptide
Lower case coding sequence of YFV17D genome, starting from amino acid #2

SEQ ID NO: 5
AGTAAATCCTGTGTGCTAATTGAGGTGCATTGGTCTGCAAATCGAGTTGCTAGGCAATAAACACATTTGG
ATTAATTTTAATCGTTCGTTGAGCGATTAGCAGAGAACTGACCAGAACATGTCTGGTCGTAAAGCTCAGG
M S G R K A Q G

SEQ ID NO: 6
GAAAAACCCTGGGCGTCAATATGGTACGACGAGGAGTTCGC*ggatcc*ATGGACATCGACCCTTATAAAGA
K T L G V N M V R R G V R G S M D I D P Y K E
ATTTGGAGCTACTGTGGAGTTACTCTCGTTTTTGCCTTCTGACTTCTTTCCTTCAGTACGAGATCTTCTA
F G A T V E L L S F L P S D F F P S V R D L L
GATACCGCCTCAGCTCTGTATCGGGAAGCCTTAGAGTCTCCTGAGCATTGTTCACCTCACCATACTGCAC
D T A S A L Y R E A L E S P E H C S P H H T A L
TCAGGCAAGCAATTCTTTGCTGGGGGGAACTAATGACTCTAGCTACCTGGGTGGGTGTTAATTTGGAAGA
R Q A I L C W G E L M T L A T W V G V N L E D
TCCAGCGTCTAGAGACCTAGTAGTCAGTTATGTCAACACTAATATGGGCCTAAAGTTCAGGCAACTCTTG
P A S R D L V V S Y V N T N M G L K F R Q L L
TGGTTTCACATTTCTTGTCTCACTTTTGGAAGAGAAACAGTTATAGAGTATTTGGTGTCTTTCGGAGTGT
W F H I S C L T F G R E T V I E Y L V S F G V W
GGATTCGCACTCCTCCAGCTTATAGACCACCAAATGCCCCTATCCTATCAACACTTCCGGAGACTACTGT
I R T P P A Y R P P N A P I L S T L P E T T V
TGTTAGACGACGAGGCAGGTCCgagggacgcgggtccctgctgacctgtggcgacgtggaggagaacccc
V R R R G R S E G R G S L L T C G D V E E N P
ggtcctagcggccgcaaagcccagggtaagacactgggcgtgaacatggttcgtcgcggcgtccggtcct
G P S G R K A Q G K T L G V N M V R R G V R S L
tgtcaaacaaaataaaacaaaaaacaaaacaaattg
S N K I K Q K T K Q I *

SEQ ID NO: 7
1 mdidpykefg asvellsflp sdffpsirdl ldtasalyre alespehcsp hhtalrqail
61 cwgelmnlat wvggnledpa sreavvsyvn vnmglkirql 1wfhiscltf gretvleylv
121 sfgvwirtpp ayrpqnapil stlpettvvr rrgr Sequence of interest of pShuttle/YFV17D/OVA
Legend:

UPPER CASE YFV17D 5′-UTR
UNDERLINED UPPER CASE coding sequence of first 21 amino acids of YFV17D capsid protein
Lower case italics BamHI site
BOLD UPPER CASE OVA coding sequence
Underlined lower case coding sequence of T2A (Thosea asigna 2A) peptide
Lower case coding sequence of YFV17D genome, starting from amino acid #2

SEQ ID NO: 8
AGTAAATCCTGTGTGCTAATTGAGGTGCATTGGTCTGCAAATCGAGTTGCTAGGCAATAAACACATTTGG
ATTAATTTTAATCGTTCGTTGAGCGATTAGCAGAGAACTGACCAGAACATGTCTGGTCGTAAAGCTCAGG

SEQ ID NO: 9
M S G R K A Q G
GAAAAACCCTGGGCGTCAATATGGTACGACGAGGAGTTCGC*ggatcc*ATGGGTAGTATCGGGGCAGCCTC
K T L G V N M V R R G V R G S M G S I G A A S
CATGGAGTTCTGCTTTGACGTATTCAAAGAGCTCAAGGTTCATCATGCTAACGAAAACATTTTTTATTGC
M E F C F D V F K E L K V H H A N E N I F Y C TABLE 1-continued Primer sequences CCCATCGCCATAATGAGTGCTCTGGCCATGGTGTATCTTGGGGCCAAAGATTCAACACGGACACAGATAA
P I A I M S A L A M V Y L G A K D S T R T Q I N
ACAAAGTAGTCCGCTTCGACAAATTGCCTGGATTTGGCGATTCTATCGAAGCTCAGTGCGGGACATCCGT
K V V R F D K L P G F G D S I E A Q C G T S V
GAATGTGCATAGTAGTCTCAGGGATATCCTCAACCAGATAACAAAACCAAATGACGTTTATTCTTTTAGC
N V H S S L R D I L N Q I T K P N D V Y S F S
CTCGCCAGTCGCCTTTATGCCGAGGAACGGTATCCCATTTTGCCAGAGTACTTGCAATGTGTAAAAGAGT
L A S R L Y A E E R Y P I L P E Y L Q C V K E L
TGTACCGAGGCGGGCTCGAACCCATTAATTTCCAGACAGCAGCAGACCAAGCAAGAGAGCTTATAAATAG
Y R G G L E P I N F Q T A A D Q A R E L I N S
CTGGGTAGAATCTCAAACTAACGGAATTATAAGAAACGTGCTCCAACCAAGTTCAGTGGATTCTCAGACA
W V E S Q T N G I I R N V L Q P S S V D S Q T
GCCATGGTCCTTGTTAATGCCATTGTTTTCAAAGGTCTTTGGGAGAAAGCATTTAAAGATGAGGATACCC
A M V L V N A I V F K G L W E K A F K D E D T Q
AGGCTATGCCCTTTCGAGTAACCGAACAAGAGAGTAAGCCCGTACAAATGATGTACCAGATAGGATTGTT
A M P F R V T E Q E S K P V Q M M Y Q I G L F
TAGAGTCGCCTCCATGGCTAGTGAGAAGATGAAGATTCTGGAGCTCCCCTTTGCCAGCGGTACAATGAGC
R V A S M A S E K M K I L E L P F A S G T M S
ATGCTTGTCCTGCTCCCTGACGAGGTGTCAGGGCTCGAACAATTGGAGAGCATTATCAACTTCGAGAAAC
M L V L L P D E V S G L E Q L E S I I N F E K L
TCACAGAATGGACTAGTAGCAATGTGATGGAGGAAAGGAAGATTAAGGTATATCTTCCACGGATGAAAAT
T E W T S S N V M E E R K I K V Y L P R M K M
GGAAGAGAAATACAATCTCACAAGCGTACTCATGGCTATGGGAATAACAGATGTGTTTTCATCCAGCGCC
E E K Y N L T S V L M A M G I T D V F S S S A
AACTTGAGCGGCATTAGCTCTGCCGAAAGTCTGAAGATTTCACAGGCCGTACATGCCGCCCACGCTGAAA
N L S G I S S A E S L K I S Q A V H A A H A E I
TAAATGAGGCTGGCAGGGAAGTAGTTGGGAGTGCAGAGGCTGGCGTAGATGCTGCCAGCGTATCCGAGGA
N E A G R E V V G S A E A G V D A A S V S E E
GTTCCGAGCCGATCACCCTTTTCTCTTTTGTATCAAACATATTGCTACTAATGCAGTCCTCTTTTTCGGT
F R A D H P F L F C I K H I A T N A V L F F G
CGGTGTGTGAGCCCAgagggacgcgggtccctgctgacctgtggcgacgtggaggagaaccccggtccta
R C V S P E G R G S L L T C G D V E E N P G P S
gcggccgcaaagcccagggtaagacactgggcgtgaacatggttcgtcgcggcgtccggtccttgtcaaa
G R K A Q G K T L G V N M V R R G V R S L S N
caaaataaaacaaaaaacaaaacaaattg
K I K Q K T K Q I SEQ ID NO: 10
1 mgsigaasme fcfdvfkelk vhhanenify cpiaimsala mvylgakdst rtqinkvvrf
61 dklpgfgdsi eaqcgtsvnv hsslrdilnq itkpndvysf slasrlyaee rypilpeylq
121 cvkelyrggl epinfqtaad qarelinswv esqtngiirn vlqpssvdsq tamvlvnaiv
181 fkglwekafk dedtqampfr vteqeskpvq mmyqiglfrv asmasekmki lelpfasgtm
241 smlvllpdev sgleqlesii nfekltewts snvmeerkik vylprmkmee kynltsvlma
301 mgitdvfsss anlsgissae slkisqavha ahaeineagr evvgsaeagv daasvseefr
361 adhpflfcik hiatnavlff grcvsp Sequence of interest of pShuttle/YFV17D/EBNA1

Legend:

| | |
|---|---|
| UPPER CASE | YFV17D 5′-UTR |
| UNDERLINED UPPER CASE | coding sequence of first 21 amino acids of YFV17D capsid protein |
| Lower case italics | BamHI site |
| BOLD UPPER CASE | EBNA1 coding sequence |
| Underlined lower case | coding sequence of T2A (Thosea asigna 2A) peptide |
| Lower case | coding sequence of YFV17D genome, starting from amino acid #2 |

SEQ ID NO: 11
AGTAAATCCTGTGTGCTAATTGAGGTGCATTGGTCTGCAAATCGAGTTGCTAGGCAATAAACACATTTGG
ATTAATTTTAATCGTTCGTTGAGCGATTAGCAGAGAACTGACCAGAACATGTCTGGTCGTAAAGCTCAGG

SEQ ID No: 12
M S G R K A Q G
GAAAAACCCTGGGCGTCAATATGGTACGACGAGGAGTTCGC*ggatcc*GGTAGAAGGCCATTTTTCCACCC
K T L G V N M V R R G V R G S G R R P F F H P
TGTAGGGGAAGCCGATTATTTTGAATACCACCAAGAAGGTGGCCCAGATGGTGAGCCTGACGTGCCCCCG
V G E A D Y F E Y H Q E G G P D G E P D V P P
GGAGCGATAGAGCAGGGCCCCGCAGATGACCCAGGAGAAGGCCCAAGCACTGGACCCCGGGGTCAGGGTG
G A I E Q G P A D D P G E G P S T G P R G Q G D
ATGGAGGCAGGCGCAAAAAAGGAGGGTGGTTTGGAAAGCATCGTGGTCAAGGAGGTTCCAACCCGAAATT
G G R R K K G G W F G K H R G Q G G S N P K F
TGAGAACATTGCAGAAGGTTTAAGAGCTCTCCTGGCTAGGAGTCACGTAGAAAGGACTACCGACGAAGGA
E N I A E G L R A L L A R S H V E R T T D E G
ACTTGGGTCGCCGGTGTGTTCGTATATGGAGGTAGTAAGACCTCCCTTTACAACCTAAGGCGAGGAACTG
T W V A G V F V Y G G S K T S L Y N L R R G T A
CCCTTGCTATTCCACAATGTCGTCTTACACCATTGAGTCGTCTCCCCTTTGGAATGGCCCCTGGACCCGG
L A I P Q C R L T P L S R L P F G M A P G P G
CCCACAACCTGGCCCGCTAAGGGAGTCCATTGTCTGTTATTTCATGGTCTTTTTACAAACTCATATATTT

TABLE 1-continued

| Primer sequences |
|---|
| P Q P G P L R E S I V C Y F M V F L Q T H I F |
| **GCTGAGGTTTTGAAGGATGCGATTAAGGACCTTGTTATGACAAAGCCCGCTCCTACCTGCAATATCAGGG** |
| A E V L K D A I K D L V M T K P A P T C N I R V |
| **TGACTGTGTGCAGCTTTGACGATGGAGTAGATTTGCCTCCCTGGTTTCCACCTATGGTGGAAGGGGCTGC** |
| T V C S F D D G V D L P P W F P P M V E G A A |
| **CGCGGAGGGTGATGACGGAGATGACGGAGATGAAGGAGGTGATGGAGATGAGGGTGAGGAAGGGCAGGAG** |
| A E G D D G D D G D E G G D G D E G E E G Q E |
| gagggacgcgggtccctgctgacctgtggcgacgtggaggagaaccccggtcctagcggccgcaaagccc |
| E G R G S L L T C G D V E E N P G P S G R K A Q |
| agggtaagacactgggcgtgaacatggttcgtcgcggcgtccggtccttgtcaaacaaaataaaacaaaa |
| G K T L G V N M V R R G V R S L S N K I K Q K |
| aacaaaacaaattg |
| T K Q I |
| |
| SEQ ID NO: 13 |
| 1 pffhpvgead yfeylqeggp dgepdvppga ieqgpaddpg egpstgprgq gdggrrkkgg |
| 61 wfgkhrgqgg snpkfeniae glrvllarsh vertteegtw vagvfvyggs ktslynlrrg |
| 121 talaipqcrl tplsrlpfgm apgpgpqpgp lresivcyfm vflqthifae vlkdaikdlv |
| 181 mtkpaptcni kvtvcsfddg vdlppwfppm vegaaaegdd gddgdeggdg degeegge |
| |
| Capsid synonymous codons sequences: |
| atgtctggtcgtaaagctcagggaaaaaccctgggcgtcaatatggtacgacgaggagttcgc |
| (SEQ ID NO: 14) |
| |
| agcggccgcaaagcccagggtaagacactgggcgtgaacatggttcgtcgcggcgtccgg. |
| (SEQ ID NO: 15) |

SEQUENCE LISTING

```
Sequence total quantity: 48
SEQ ID NO: 1           moltype = DNA  length = 1744
FEATURE                Location/Qualifiers
misc_feature           1..1744
                       note = 5' end ofYFV with heterologous antigen
source                 1..1744
                       mol_type = other DNA
                       organism = synthetic construct
SEQUENCE: 1
agtaaatcct gtgtgctaat tgaggtgcat tggtctgcaa atcgagttgc taggcaataa  60
acacatttgg attaatttta atcgttcgtt gagcgattag cagagaactg accagaacat  120
gtctggtcgt aaagctcagg gaaaaaccct gggcgtcaat atggtacgac gaggagttcg  180
cggatccgtt taaacctcgt ccccgccggg tcacccggcc agcgacatgg aggcccagaa  240
taccctcctt gacagtcttg acgtgcgcag ctcaggggca tgatgtgact gtcgcccgta  300
catttagccc atacatcccc atgtataatc atttgcatcc atacattttg atggccgcac  360
ggcgcgaagc aaaaattacg gctcctcgct gcagacctgc gagcagggaa acgctcccct  420
cacagacgcg ttgaattgtc cccacgccgc gcccctgtag agaaatataa aaggttagga  480
tttgccactg aggttcttct ttcatatact tccttttaaa atcttgctag gatacagttc  540
tcacatcaca tccgaacata aacaaccatg acagtcaaca ctaagaccta tagtgagaga  600
gcagaaactc atgcctcacc agtagcacaa cgattatttc gattaatgga actgaagaaa  660
accaatttat gtgcatcaat tgatgttgat accactaagg aattccttga attaattgat  720
aaattgggtc cttatgtatg cttaatcaag actcatattg atataatcaa tgattttcc  780
tatgaatcca ctattgaacc attattagaa ctttcacgta aacatcaatt tatgattttt  840
gaagatagaa aatttgctga tattggtaat accgtgaaga aacaatatat tggtggagtt  900
tataaaatta gtagttgggc agatattact aatgctcatg gtgtcactgg gaatggagta  960
gttgaaggat taaaacaggg agctaaagaa accaccacca accaagagcc aagagggtta  1020
ttgatgttag ctgaattatc atcagtggga tcattagcat atggagaata ttctcaaaaa  1080
actgttgaaa ttgctaaatc cgataaggaa tttgttattg gatttattgc ccaacgtgat  1140
atgggtggac aagaagaagg atttgattgg cttattatga cacctggagt tggattagat  1200
gataaaggtg atggattagg acaacaatat agaactgttg atgaagttgt tagcactgga  1260
actgatatta tcattgttgg tagaggattg tttggtaaag gaagagatcc agatattgaa  1320
ggtaaaaggt atagagatgc tggttggaat gcttatttga aaaagactgg ccaattataa  1380
tcagtactga caataaaaag attcttgttt tcaagaactt gtcatttgta tagtttttt  1440
atattgtagt tgttctattt taatcaaatg ttagcgtgat ttatattttt tttcgcctcg  1500
acatcatctg cccagatgcg aagttaagtg cgcagaaagt aatatcatgc gtcaatcgta  1560
tgtgaatgct ggtcgctata ctgtttaaac gagggacgcg ggtccctgct gacctgtggc  1620
gacgtggagg agaaccccgg tcctagcggc cgcaaagccc agggtaagac actgggcgtg  1680
aacatggttc gtcgcggcgt ccggtccttg tcaaacaaaa taaaacaaaa aacaaaacaa  1740
attg                                                               1744

SEQ ID NO: 2           moltype = AA  length = 21
FEATURE                Location/Qualifiers
REGION                 1..21
                       note = N terminal part of capsid
```

-continued

```
source                  1..21
                        mol_type = protein
                        organism = synthetic construct
SEQUENCE: 2
MSGRKAQGKT LGVNMVRRGV R                                            21

SEQ ID NO: 3            moltype = AA  length = 270
FEATURE                 Location/Qualifiers
REGION                  1..270
                        note = Hepatitis antigen
source                  1..270
                        mol_type = protein
                        organism = synthetic construct
SEQUENCE: 3
MTVNTKTYSE RAETHASPVA QRLFRLMELK KTNLCASIDV DTTKEFLELI DKLGPYVCLI  60
KTHIDIINDF SYESTIEPLL ELSRKHQFMI FEDRKFADIG NTVKKQYIGG VYKISSWADI  120
TNAHGVTGNG VVEGLKQGAK ETTTNQEPRG LLMLAELSSV GSLAYGEYSQ KTVEIAKSDK  180
EFVIGFIAQR DMGGQEEGFD WLIMTPGVGL DDKGDGLGQQ YRTVDEVVST GTDIIIVGRG  240
LFGKGRDPDI EGKRYRDAGW NAYLKKTGQL                                   270

SEQ ID NO: 4            moltype = AA  length = 51
FEATURE                 Location/Qualifiers
REGION                  1..51
                        note = 2A peptide + N terminal part of capsid protein
source                  1..51
                        mol_type = protein
                        organism = synthetic construct
SEQUENCE: 4
EGRGSLLTCG DVEENPGPSG RKAQGKTLGV NMVRRGVRSL SNKIKQKTKQ I            51

SEQ ID NO: 5            moltype = DNA  length = 806
FEATURE                 Location/Qualifiers
misc_feature            1..806
                        note = YF17D based constructs with hepatitis antigen
source                  1..806
                        mol_type = other DNA
                        organism = synthetic construct
SEQUENCE: 5
agtaaatcct gtgtgctaat tgaggtgcat tggtctgcaa atcgagttgc taggcaataa  60
acacatttgg attaatttta atcgttcgtt gagcgattag cagagaactg accagaacat  120
gtctggtcgt aaagctcagg gaaaaaccct gggcgtcaat atggtacgac gaggagttcg  180
cggatccatg gacatcgacc cttataaaga atttggagct actgtggagt tactctcgtt  240
tttgccttct gacttctttc cttcagtacg agatcttcta gataccgcct cagctctgta  300
tcgggaagcc ttagagtctc ctgagcattg ttcacctcac catactgcac tcaggcaagc  360
aattctttgc tgggggggaac taatgactct agctacctgg gtgggtgtta atttggaaga  420
tccagcgtct agagacctag tagtcagtta tgtcaacact aatatgggcc taaagttcag  480
gcaactcttg tggtttcaca tttcttgtct cacttttgga agagaaacag ttatagagta  540
tttggtgtct ttcggagtgt ggattcgcac tcctccagct tatagaccac caaatgcccc  600
tatcctatca acacttccgg agactactgt tgttagacga cgaggcaggt ccgagggacg  660
cgggtccctg ctgacctgtg gcgacgtgga ggagaacccc ggtcctagcg gccgcaaagc  720
ccagggtaag acactgggcg tgaacatggt tcgtcgcggc gtccggtcct tgtcaaacaa  780
aataaaacaa aaaacaaaac aaattg                                       806

SEQ ID NO: 6            moltype = AA  length = 229
FEATURE                 Location/Qualifiers
REGION                  1..229
                        note = YFV based construct with hepatitis antigen
source                  1..229
                        mol_type = protein
                        organism = synthetic construct
SEQUENCE: 6
MSGRKAQGKT LGVNMVRRGV RGSMDIDPYK EFGATVELLS FLPSDFFPSV RDLLDTASAL  60
YREALESPEH CSPHHTALRQ AILCWGELMT LATWVGVNLE DPASRDLVVS YVNTNMGLKF  120
RQLLWFHISC LTFGRETVIE YLVSFGVWIR TPPAYRPPNA PILSTLPETT VVRRRGRSEG  180
RGSLLTCGDV EENPGPSGRK AQGKTLGVNM VRRGVRSLSN KIKQKTKQI              229

SEQ ID NO: 7            moltype = AA  length = 154
FEATURE                 Location/Qualifiers
REGION                  1..154
                        note = Hepatis B antigen sequence
source                  1..154
                        mol_type = protein
                        organism = synthetic construct
SEQUENCE: 7
MDIDPYKEFG ASVELLSFLP SDFFPSIRDL LDTASALYRE ALESPEHCSP HHTALRQAIL  60
CWGELMNLAT WVGGNLEDPA SREAVVSYVN VNMGLKIRQL LWFHISCLTF GRETVLEYLV  120
SFGVWIRTPP AYRPQNAPIL STLPETTVVR RRGR                              154

SEQ ID NO: 8            moltype = DNA  length = 1429
```

-continued

```
FEATURE                 Location/Qualifiers
misc_feature            1..1429
                        note = YFV based construct with ovalbumin
source                  1..1429
                        mol_type = other DNA
                        organism = synthetic construct
SEQUENCE: 8
agtaaatcct gtgtgctaat tgaggtgcat tggtctgcaa atcgagttgc taggcaataa  60
acacatttgg attaatttta atcgttcgtt gagcgattag cagagaactg accagaacat  120
gtctggtcgt aaagctcagg gaaaaaccct gggcgtcaat atggtacgac gaggagttcg  180
cggatccatg ggtagtatcg gggcagcctc catggagttc tgctttgacg tattcaaaga  240
gctcaaggtt catcatgcta acgaaaacat tttttattgc cccatcgcca taatgagtgc  300
tctggccatg gtgtatcttg gggccaaaga ttcaacacgg acacagataa acaaagtagt  360
ccgcttcgac aaattgcctg gatttggcga ttctatcgaa gctcagtgcg ggacatccgt  420
gaatgtgcat agtagtctca gggatatcct caaccagata acaaaaccaa atgacgttta  480
ttcttttagc ctcgccagtc gcctttatgc cgaggaacgg tatcccattt tgccagagta  540
cttgcaatgt gtaaaagagt tgtaccgagg cgggctcgaa cccattaatt tccagacagc  600
agcagaccaa gcaagagagc ttataaatag ctgggtagaa tctcaaacta acggaattat  660
aagaaacgtg ctccaaccaa gttcagtgga ttctcagaca gccatggtcc ttgttaatgc  720
cattgttttc aaaggtcttt gggagaaagc atttaaagat gaggataccc aggctatgcc  780
ctttcgagta accgaacaag agagtaagcc cgtacaaatg atgtaccaga taggattgtt  840
tagagtcgcc tccatggcta gtgagaagat gaagattctg gagctcccct ttgccagcgg  900
tacaatgagc atgcttgtcc tgctccctga cgaggtgtca gggctcgaac aattggagag  960
cattatcaac ttcgagaaac tcacagaatg gactagtagc aatgtgatgg aggaaaggaa  1020
gattaaggta tatcttccac ggatgaaaat ggaagagaaa tacaatctca caagcgtact  1080
catggctatg ggaataacag atgtgttttc atccagcgcc aacttgagcg gcattagctc  1140
tgccgaaagt ctgaagattt cacaggccgt acatgccgcc cacgctgaaa taaatgaggc  1200
tggcagggaa gtagttggga gtgcagaggc tggcgtagat gctgccagcg tatccgagga  1260
gttccgagcc gatcaccctt ttctcttttg tatcaaacat attgctacta atgcagtcct  1320
ctttttcggt cggtgtgtga gcccagaggg acgcgggtcc ctgctgacct gtggcgacgt  1380
ggaggagaac cccggtccta caaaataaaa caaaaaacaa aacaaattg             1429

SEQ ID NO: 9            moltype = AA  length = 460
FEATURE                 Location/Qualifiers
REGION                  1..460
                        note = YFV based construct with ovalbumin
source                  1..460
                        mol_type = protein
                        organism = synthetic construct
SEQUENCE: 9
MSGRKAQGKT LGVNMVRRGV RGSMGSIGAA SMEFCFDVFK ELKVHHANEN IFYCPIAIMS  60
ALAMVYLGAK DSTRTQINKV VRFDKLPGFG DSIEAQCGTS VNVHSSLRDI LNQITKPNDV  120
YSFSLASRLY AEERYPILPE YLQCVKELYR GGLEPINFQT AADQARELIN SWVESQTNGI  180
IRNVLQPSSV DSQTAMVLVN AIVFKGLWEK AFKDEDTQAM PFRVTEQESK PVQMMYQIGL  240
FRVASMASEK MKILELPFAS GTMSMLVLLP DEVSGLEQLE SIINFEKLTE WTSSNVMEER  300
KIKVYLPRMK MEEKYNLTSV LMAMGITDVF SSSANLSGIS SAESLKISQA VHAAHAEINE  360
AGREVVGSAE AGVDAASVSE EFRADHPFLF CIKHIATNAV LFFGRCVSPE GRGSLLTCGD  420
VEENPGPSGR KAQGKTLGVN MVRRGVRSLS NKIKQKTKQI                       460

SEQ ID NO: 10           moltype = AA  length = 386
FEATURE                 Location/Qualifiers
source                  1..386
                        mol_type = protein
                        organism = Gallus gallus
SEQUENCE: 10
MGSIGAASME FCFDVFKELK VHHANENIFY CPIAIMSALA MVYLGAKDST RTQINKVVRF  60
DKLPGFGDSI EAQCGTSVNV HSSLRDILNQ ITKPNDVYSF SLASRLYAEE RYPILPEYLQ  120
CVKELYRGGL EPINFQTAAD QARELINSWV ESQTNGIIRN VLQPSSVDSQ TAMVLVNAIV  180
FKGLWEKAFK DEDTQAMPFR VTEQESKPVQ MMYQIGLFRV ASMASEKMKI LELPFASGTM  240
SMLVLLPDEV SGLEQLESII NFEKLTEWTS SNVMEERKIK VYLPRMKMEE KYNLTSVLMA  300
MGITDVFSSS ANLSGISSAE SLKISQAVHA AHAEINEAGR EVVGSAEAGV DAASVSEEFR  360
ADHPFLFCIK HIATNAVLFF GRCVSP                                       386

SEQ ID NO: 11           moltype = DNA  length = 1064
FEATURE                 Location/Qualifiers
misc_feature            1..1064
                        note = YFV based constuct with EBNA 1 antigen
source                  1..1064
                        mol_type = other DNA
                        organism = synthetic construct
SEQUENCE: 11
agtaaatcct gtgtgctaat tgaggtgcat tggtctgcaa atcgagttgc taggcaataa  60
acacatttgg attaatttta atcgttcgtt gagcgattag cagagaactg accagaacat  120
gtctggtcgt aaagctcagg gaaaaaccct gggcgtcaat atggtacgac gaggagttcg  180
cggatccggt agaaggccat ttttccaccc tgtaggggaa gccgattatt ttgaatacca  240
ccaagaaggt ggcccagatg gtgagcctga cgtgcccccg ggagcgatag agcagggccc  300
cgcagatgac ccaggagaag gcccaagcac tggaccccgg ggtcagggtg atggaggcag  360
gcgcaaaaaa ggagggtggt ttggaaagca tcgtggtcaa ggaggttcca acccgaaatt  420
tgagaacatt gcagaaggtt taagagctct cctggctagg agtcacgtag aaaggactac  480
```

-continued

```
cgacgaagga acttgggtcg ccggtgtgtt cgtatatgga ggtagtaaga cctcccttta  540
caacctaagg cgaggaactg cccttgctat tccacaatgt cgtcttacac cattgagtcg  600
tctccccttt ggaatggccc ctggacccgg cccacaacct ggcccgctaa gggagtccat  660
tgtctgttat ttcatggtct ttttacaaac tcatatattt gctgaggttt tgaaggatgc  720
gattaaggac cttgttatga caaagcccgc tcctacctgc aatatcaggg tgactgtgtg  780
cagctttgac gatggagtag atttgcctcc ctggtttcca cctatggtgg aaggggctgc  840
cgcggagggt gatgacggag atgacggaga tgaaggaggt gatggagatg agggtgagga  900
agggcaggag gagggacgcg ggtccctgct gacctgtggc gacgtggagg agaaccccgg  960
tcctagcggc cgcaaagccc agggtaagac actgggcgtg aacatggttc gtcgcggcgt  1020
ccggtccttg tcaaacaaaa taaaacaaaa aacaaaacaa attg                  1064

SEQ ID NO: 12          moltype = AA  length = 315
FEATURE                Location/Qualifiers
REGION                 1..315
                       note = YVF based construct with EBNA1 antigen
source                 1..315
                       mol_type = protein
                       organism = synthetic construct
SEQUENCE: 12
MSGRKAQGKT LGVNMVRRGV RGSGRRPFFH PVGEADYFEY HQEGGPDGEP DVPPGAIEQG  60
PADDPGEGPS TGPRGQGDGG RRKKGGWFGK HRGQGGSNPK FENIAEGLRA LLARSHVERT  120
TDEGTWVAGV FVYGGSKTSL YNLRRGTALA IPQCRLTPLS RLPFGMAPGP GPQPGPLRES  180
IVCYFMVFLQ THIFAEVLKD AIKDLVMTKP APTCNIRVTV CSFDDGVDLP PWFPPMVEGA  240
AAEGDDGDDG DEGGDGDEGE EGQEEGRGSL LTCGDVEENP GPSGRKAQGK TLGVNMVRRG  300
VRSLSNKIKQ KTKQI                                                   315

SEQ ID NO: 13          moltype = AA  length = 238
FEATURE                Location/Qualifiers
REGION                 1..238
                       note = EBNA1 antigen
source                 1..238
                       mol_type = protein
                       organism = synthetic construct
SEQUENCE: 13
PFFHPVGEAD YFEYLQEGGP DGEPDVPPGA IEQGPADDPG EGPSTGPRGQ GDGGRRKKGG  60
WFGKHRGQGG SNPKFENIAE GLRVLLARSH VERTTEEGTW VAGVFVYGGS KTSLYNLRRG  120
TALAIPQCRL TPLSRLPFGM APGPGPQPGP LRESIVCYFM VFLQTHIFAE VLKDAIKDLV  180
MTKPAPTCNI KVTVCSFDDG VDLPPWFPPM VEGAAAEGDD GDDGDEGGDG DEGEEGQE    238

SEQ ID NO: 14          moltype = DNA  length = 63
FEATURE                Location/Qualifiers
misc_feature           1..63
                       note = cDNA for YFV capsid nterminal fragment
source                 1..63
                       mol_type = other DNA
                       organism = synthetic construct
SEQUENCE: 14
atgtctggtc gtaaagctca gggaaaaacc ctgggcgtca atatggtacg acgaggagtt  60
cgc                                                               63

SEQ ID NO: 15          moltype = DNA  length = 60
FEATURE                Location/Qualifiers
misc_feature           1..60
                       note = cDNA for capsid nterminal fragment
source                 1..60
                       mol_type = other DNA
                       organism = synthetic construct
SEQUENCE: 15
agcggccgca aagcccaggg taagacactg ggcgtgaaca tggttcgtcg cggcgtccgg  60

SEQ ID NO: 16          moltype = AA  length = 18
FEATURE                Location/Qualifiers
source                 1..18
                       mol_type = protein
                       organism = Thosea asigna
SEQUENCE: 16
EGRGSLLTCG DVEENPGP                                               18

SEQ ID NO: 17          moltype = AA  length = 12
FEATURE                Location/Qualifiers
REGION                 1..12
                       note = viral 2A cleaving peptide
REGION                 2..4
                       note = misc_feature - Xaa can be any naturally occurring
                        amino acid
SITE                   9
                       note = misc_feature - Xaa can be any naturally occurring
                        amino acid
source                 1..12
```

```
                        mol_type = protein
                        organism = synthetic construct
SEQUENCE: 17
LXXXGDVEXP GP                                                      12

SEQ ID NO: 18           moltype = AA  length = 13
FEATURE                 Location/Qualifiers
source                  1..13
                        mol_type = protein
                        organism = Thosea asigna
SEQUENCE: 18
LLTCGDVEEN PGP                                                     13

SEQ ID NO: 19           moltype = DNA  length = 56
FEATURE                 Location/Qualifiers
misc_feature            1..56
                        note = pcr primer
source                  1..56
                        mol_type = other DNA
                        organism = synthetic construct
SEQUENCE: 19
aagctcaggg aaaaaccctg ggcgtcaata tggtacgacg aggagttcgc ggatcc      56

SEQ ID NO: 20           moltype = DNA  length = 60
FEATURE                 Location/Qualifiers
misc_feature            1..60
                        note = pcr primer
source                  1..60
                        mol_type = other DNA
                        organism = synthetic construct
SEQUENCE: 20
gtgtcttacc ctgggctttg cggccgctag gaccggggtt ctcctccacg tcgccacagg  60

SEQ ID NO: 21           moltype = DNA  length = 60
FEATURE                 Location/Qualifiers
misc_feature            1..60
                        note = pcr primer
source                  1..60
                        mol_type = other DNA
                        organism = synthetic construct
SEQUENCE: 21
gtcaatatgg tacgacgagg agttcgcgga tccgtttaaa cctcgtcccc gccgggtcac  60

SEQ ID NO: 22           moltype = DNA  length = 60
FEATURE                 Location/Qualifiers
misc_feature            1..60
                        note = pcr primer
source                  1..60
                        mol_type = other DNA
                        organism = synthetic construct
SEQUENCE: 22
gtcgccacag gtcagcaggg acccgcgtcc ctcgtttaaa cagtatagcg accagcattc  60

SEQ ID NO: 23           moltype = DNA  length = 60
FEATURE                 Location/Qualifiers
misc_feature            1..60
                        note = pcr primer
source                  1..60
                        mol_type = other DNA
                        organism = synthetic construct
SEQUENCE: 23
cagaacatgt ctggtcgtaa agctcaggga aaaaccctgg gcgtcaatat ggtacgacga  60

SEQ ID NO: 24           moltype = DNA  length = 60
FEATURE                 Location/Qualifiers
misc_feature            1..60
                        note = pcr primer
source                  1..60
                        mol_type = other DNA
                        organism = synthetic construct
SEQUENCE: 24
accctgggct ttgcggccgc taggaccggg gttctcctcc acgtcgccac aggtcagcag  60

SEQ ID NO: 25           moltype = DNA  length = 60
FEATURE                 Location/Qualifiers
misc_feature            1..60
                        note = pcr primer
source                  1..60
                        mol_type = other DNA
```

```
                          organism = synthetic construct
SEQUENCE: 25
ccggacgccg cgacgaacca tgttcacgcc cagtgtctta ccctgggctt tgcggccgct  60

SEQ ID NO: 26             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 26
cctgggcgtc aatatggtac gacgaggagt tcgcggatcc atggacatcg acccttataa  60

SEQ ID NO: 27             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 27
cctccacgtc gccacaggtc agcagggacc cgcgtccctc cgcgagggcc tttccctcgg  60

SEQ ID NO: 28             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 28
gtcttaccct gggctttgcg gccgctagga ccggggttct cctccacgtc gccacaggtc  60

SEQ ID NO: 29             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 29
tggaggagaa ccccggtcct agcggccgca aagcccaggg taagacactg ggcgtgaaca  60

SEQ ID NO: 30             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 30
taagacactg ggcgtgaaca tggttcgtcg cggcgtccgg tccttgtcaa acaaaataaa  60

SEQ ID NO: 31             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 31
tgacgcccag ggtttttccc tgagctttac gaccagacat gttctggtca gttctctgct  60

SEQ ID NO: 32             moltype = DNA  length = 60
FEATURE                   Location/Qualifiers
misc_feature              1..60
                          note = pcr primer
source                    1..60
                          mol_type = other DNA
                          organism = synthetic construct
SEQUENCE: 32
tcgatgtcca tggatccgcg aactcctcgt cgtaccatat tgacgcccag ggtttttccc  60

SEQ ID NO: 33             moltype = DNA  length = 57
FEATURE                   Location/Qualifiers
misc_feature              1..57
                          note = pcr primer
source                    1..57
```

-continued

```
                         mol_type = other DNA
                         organism = synthetic construct
SEQUENCE: 33
tggattaatt ttaatcgttc gttgagcgat tagcagagaa ctgaccagaa catgtct     57

SEQ ID NO: 34            moltype = DNA  length = 57
FEATURE                  Location/Qualifiers
misc_feature             1..57
                         note = pcr primer
source                   1..57
                         mol_type = other DNA
                         organism = synthetic construct
SEQUENCE: 34
cctccacgtc gccacaggtc agcagggacc cgcgtccctc ggacctgcct cgtcgtc     57

SEQ ID NO: 35            moltype = DNA  length = 60
FEATURE                  Location/Qualifiers
misc_feature             1..60
                         note = pcr primer
source                   1..60
                         mol_type = other DNA
                         organism = synthetic construct
SEQUENCE: 35
tgtttccaat ttgttttgtt ttttgtttta ttttgtttga caaggaccgg acgccgcgac  60

SEQ ID NO: 36            moltype = DNA  length = 60
FEATURE                  Location/Qualifiers
misc_feature             1..60
                         note = pcr primer
source                   1..60
                         mol_type = other DNA
                         organism = synthetic construct
SEQUENCE: 36
gggcgtcaat atggtacgac gaggagttcg cggatccatg ggtagaaggc catttttcca  60

SEQ ID NO: 37            moltype = DNA  length = 60
FEATURE                  Location/Qualifiers
misc_feature             1..60
                         note = pcr primer
source                   1..60
                         mol_type = other DNA
                         organism = synthetic construct
SEQUENCE: 37
cctccacgtc gccacaggtc agcagggacc cgcgtccctc ctcctgccct tcctcaccct  60

SEQ ID NO: 38            moltype = AA  length = 24
FEATURE                  Location/Qualifiers
source                   1..24
                         mol_type = protein
                         organism = Foot-and-mouth disease virus
SEQUENCE: 38
APVKQTLNFD LLKLAGDVES NPGP                                         24

SEQ ID NO: 39            moltype = AA  length = 19
FEATURE                  Location/Qualifiers
source                   1..19
                         mol_type = protein
                         organism = Porcine teschovirus-1
SEQUENCE: 39
ATNFSLLKQA GDVEENPGP                                               19

SEQ ID NO: 40            moltype = AA  length = 20
FEATURE                  Location/Qualifiers
source                   1..20
                         mol_type = protein
                         organism = equine rhinitis A virus
SEQUENCE: 40
QCTNYALLKL AGDVESNPGP                                              20

SEQ ID NO: 41            moltype = AA  length = 29
FEATURE                  Location/Qualifiers
REGION                   1..29
                         note = Yellow fever capsid fragment + Hbc fragment
source                   1..29
                         mol_type = protein
                         organism = synthetic construct
SEQUENCE: 41
MSGRKAQGKT LGVNMVRRGV RGSMDIDPY                                    29
```

-continued

```
SEQ ID NO: 42          moltype = AA  length = 30
FEATURE                Location/Qualifiers
REGION                 1..30
                       note = Hbc fragment - T2A peptide - Yeloow fever fragment
source                 1..30
                       mol_type = protein
                       organism = synthetic construct
SEQUENCE: 42
RRRGRSEGRG SLLTCGDVEE NPGPSGRKAQ                                    30

SEQ ID NO: 43          moltype = DNA  length = 63
FEATURE                Location/Qualifiers
source                 1..63
                       mol_type = other DNA
                       organism = Yellow fever virus
SEQUENCE: 43
atgtctggtc gtaaagctca gggaaaaacc ctgggcgtca atatggtacg acgaggagtt  60
cgc                                                                 63

SEQ ID NO: 44          moltype = DNA  length = 58
FEATURE                Location/Qualifiers
misc_feature           1..58
                       note = codon modified YFV capsid
source                 1..58
                       mol_type = other DNA
                       organism = synthetic construct
SEQUENCE: 44
cggccgcaaa gcccagggta agacactggg cgtgaacatg gttcgtcgcg gcgtccgg    58

SEQ ID NO: 45          moltype = AA  length = 21
FEATURE                Location/Qualifiers
source                 1..21
                       mol_type = protein
                       organism = Yellow fever virus
SEQUENCE: 45
MSGRKAQGKT LGVNMVRRGV R                                             21

SEQ ID NO: 46          moltype = AA  length = 8
FEATURE                Location/Qualifiers
REGION                 1..8
                       note = 2A peptide consensus sequence
SITE                   2
                       note = misc_feature - Xaa can be any naturally occurring
                        amino acid
SITE                   4
                       note = misc_feature - Xaa can be any naturally occurring
                        amino acid
source                 1..8
                       mol_type = protein
                       organism = synthetic construct
SEQUENCE: 46
DXEXNPGP                                                            8

SEQ ID NO: 47          moltype = AA  length = 4
FEATURE                Location/Qualifiers
REGION                 1..4
                       note = 2A cleavage site
source                 1..4
                       mol_type = protein
                       organism = synthetic construct
SEQUENCE: 47
NPGP                                                                4

SEQ ID NO: 48          moltype = AA  length = 5
FEATURE                Location/Qualifiers
REGION                 1..5
                       note = 2A cleavage site
source                 1..5
                       mol_type = protein
                       organism = synthetic construct
SEQUENCE: 48
NPGPS                                                               5
```

The invention claimed is:

1. A polynucleotide comprising a nucleotide sequence encoding a flavivirus wherein the nucleotide sequence encoding the flavivirus is preceded by a sequence encoding:

a part of a flavivirus capsid protein comprising or consisting of an N terminal part of the flavivirus capsid protein, an immunogenic core antigen of hepatitis B virus (HBC), and a 2A cleaving peptide.

2. The polynucleotide according to claim 1, wherein the part of the flavivirus capsid protein comprises or consists of 21 N terminal amino acids of the flavivirus capsid protein.

3. The polynucleotide according to claim 1, wherein the nucleotide sequence encoding the N terminal part of the flavivirus capsid protein has one or more synonymous codons compared with the corresponding sequence in the nucleotide sequence encoding the flavivirus.

4. The polynucleotide according to claim 1, wherein the flavivirus encoded by the nucleotide sequence is a Yellow Fever virus; and wherein the flavivirus capsid protein is from Yellow Fever virus.

5. The polynucleotide according to claim 4, where the N terminal part of the Yellow Fever virus capsid consists of the sequence MSGRKAQGKTLGVNMVRRGVR (SEQ ID NO: 2).

6. The polynucleotide according to claim 1, wherein the 2A cleaving peptide comprises the sequence DXEXNPGP (SEQ ID NO: 46).

7. The polynucleotide according to claim 1, wherein the 2A cleaving peptide comprises the sequence LXXXGDVEXNPGP (SEQ ID NO: 17).

8. The polynucleotide according to claim 7, wherein the 2A cleaving peptide comprises the sequence LLTCGDVEENPGP (SEQ ID NO: 18).

9. The polynucleotide according to claim 8, wherein the 2A cleaving peptide is a *Thosea asigna* 2A peptide with an amino acid sequence EGRGSLLTCGDVEENPGP (SEQ ID NO: 16).

10. The polynucleotide according to claim 1, wherein the amino acid C terminal of the 2A cleaving peptide is Gly, Ala, Ser or Thr.

11. The polynucleotide according to claim 1, wherein the immunogenic core antigen is a T cell antigen and comprises a T cell epitope.

12. The polynucleotide according to claim 1, wherein the nucleotide sequence encoding the part of the flavivirus capsid protein is located 5' of the sequence encoding said immunogenic core antigen and has a nucleotide sequence of a wild type flavivirus.

13. The polynucleotide according to claim 1, wherein a codon usage of the immunogenic core antigen is adapted for expression in bacteria.

14. The polynucleotide according to claim 3, wherein the sequences with synonymous codons are selected from:

atgtctggtcgtaaagctcagggaaaaaccctgggcgtcaatatggtacgacgaggagttcgc (SEQ ID NO: 14) and agcggccgcaaagcccagggtaagacactgggcgtgaacatggttcgtcgcggcgtccgg (SEQ ID NO: 15).

15. The polynucleotide according to claim 4, wherein the Yellow Fever virus is YF-17D attenuated virus.

16. The polynucleotide according to claim 1, which is a Bacterial Artificial Chromosome (BAC).

17. The polynucleotide according to claim 16, wherein the BAC comprises an inducible bacterial ori sequence for amplification of said BAC to more than 10 copies per bacterial cell, and a viral expression cassette comprising a cDNA of said polynucleotide and comprising cis-regulatory elements for transcription of said viral cDNA in mammalian cells and for processing of transcribed RNA into infectious RNA virus.

18. The polynucleotide according to claim 11, wherein the encoded T cell antigen comprises the amino acid sequence of SEQ ID NO: 3.

19. The polynucleotide according to claim 11, wherein the encoded T cell antigen comprises the amino acid sequence of SEQ ID NO: 7.

20. A flavivirus fusion construct comprising a flavivirus amino acid sequence wherein the flavivirus amino acid sequence is preceded at its aminoterminus by:

a part of a flavivirus capsid protein comprising or consisting of an N terminal part of the flavivirus capsid protein, an immunogenic core antigen of hepatitis B virus (HBC), and a 2A cleaving peptide.

21. The flavivirus fusion construct according to claim 20, wherein the part of the flavivirus capsid protein comprises or consists of 21 N terminal amino acids of the flavivirus capsid protein.

22. The flavivirus fusion construct according to claim 20, wherein the flavivirus amino acid sequence is from Yellow Fever virus; and wherein the flavivirus capsid protein is from Yellow Fever virus.

23. The flavivirus fusion construct according to claim 22, where the N terminal part of the Yellow Fever virus capsid consists of the sequence MSGRKAQGKTLGVNMVRRGVR (SEQ ID NO: 2).

24. The flavivirus fusion construct according to claim 20, wherein the 2A cleaving peptide comprises the sequence DXEXNPGP (SEQ ID NO: 46).

25. The flavivirus fusion construct according to claim 20, wherein the 2A cleaving peptide comprises the sequence LXXXGDVEXNPGP (SEQ ID NO: 17).

26. The flavivirus fusion construct according to claim 25, wherein the 2A cleaving peptide comprises the sequence LLTCGDVEENPGP (SEQ ID NO: 18).

27. The flavivirus fusion construct according to claim 26, wherein the 2A cleaving peptide is a *Thosea asigna* 2A peptide with an amino acid sequence EGRGSLLTCGDVEENPGP (SEQ ID NO: 16).

28. The flavivirus fusion construct according to claim 20, wherein the amino acid C terminal of the 2A cleaving peptide is Gly, Ala, Ser or Thr.

29. The flavivirus fusion construct according to claim 20, wherein the immunogenic core antigen is a T cell antigen and comprises a T cell epitope.

30. The flavivirus fusion construct according to claim 22, wherein the Yellow Fever virus is YF-17D attenuated virus.

31. The flavivirus fusion construct according to claim 20, wherein the HBC antigen comprises the amino acid sequence of SEQ ID NO: 7.

32. A vaccine comprising the polynucleotide according to claim 1, and an adjuvant.

33. The vaccine according to claim 32, wherein the vaccine provokes an immune response to a hepatitis B virus.

34. The vaccine according to claim 32, wherein the vaccine simultaneously provokes an immune response to (a) a hepatitis B virus, and (b) a flavivirus.

35. A vaccine comprising the flavivirus fusion construct according to claim 20, and an adjuvant.

36. The vaccine according to claim 35, wherein the vaccine provokes an immune response to a hepatitis B virus.

37. The vaccine according to claim 35, wherein the vaccine simultaneously provokes an immune response to (a) a hepatitis B virus, and (b) a flavivirus.

38. A pharmaceutical composition comprising the polynucleotide according to claim 1, and a pharmaceutical acceptable carrier.

39. A pharmaceutical composition comprising the flavivirus fusion construct according to claim 20, and a pharmaceutical acceptable carrier.

40. A method of preparing a vaccine against an immunogenic core antigen of hepatitis B virus (HBC), comprising the steps of:

(a) providing a Bacterial Artificial Chromosome (BAC) which comprises an inducible bacterial ori sequence for amplification of said BAC to more than 10 copies per bacterial cell, and a viral expression cassette comprising a cDNA of a polynucleotide according to claim 1, and comprising cis-regulatory elements for transcription of said cDNA in mammalian cells and for processing of transcribed RNA into infectious RNA virus, (b) transfecting mammalian cells with the BAC of step (a), (c) validating replicated virus of the transfected cells of step (b) for virulence and capacity of generating antibodies against said T cell antigen, (d) cloning the virus validated in step (c) into a vector, and (e) formulating the vector into a vaccine formulation.

41. The method according to claim 40, wherein the vector is a BAC, which comprises an inducible bacterial ori sequence for amplification of said BAC to more than 10 copies per bacterial cell.

42. A method of provoking an immune response to an immunogenic core antigen of hepatitis B virus (HBC), comprising the step of administering an effective amount of the polynucleotide according to claim 1 to a subject in need thereof.

43. A method for the therapeutic immunization of a human subject in need thereof, comprising the step of administering an effective amount of the polynucleotide of claim 1 to the subject, wherein the therapeutic immunization is against an immunogenic core antigen of hepatitis B virus.

* * * * *